US009143858B2

(12) United States Patent
Alves et al.

(10) Patent No.: US 9,143,858 B2
(45) Date of Patent: Sep. 22, 2015

(54) USER DESIGNED ACTIVE NOISE CANCELLATION (ANC) CONTROLLER FOR HEADPHONES

(71) Applicant: CSR TECHNOLOGY INC., San Jose, CA (US)

(72) Inventors: Rogerio Guedes Alves, Macomb, MI (US); Walter Andrés Zuluaga, Rochester Hills, MI (US)

(73) Assignee: CSR Technology Inc., San Jose, CA (US)

(*) Notice: Subject to any disclaimer, the term of this patent is extended or adjusted under 35 U.S.C. 154(b) by 155 days.

(21) Appl. No.: 14/109,692

(22) Filed: Dec. 17, 2013

(65) Prior Publication Data

US 2014/0105412 A1 Apr. 17, 2014

Related U.S. Application Data

(63) Continuation-in-part of application No. 13/434,350, filed on Mar. 29, 2012.

(51) Int. Cl.
*A61F 11/06* (2006.01)
*H04R 3/00* (2006.01)
(Continued)

(52) U.S. Cl.
CPC ............ *H04R 3/002* (2013.01); *G10K 11/1784* (2013.01); *G10K 2210/3033* (2013.01); (Continued)

(58) Field of Classification Search
CPC ....................... G10K 11/1788; G10K 11/1784
USPC ........................................................ 381/71.1
See application file for complete search history.

(56) References Cited

U.S. PATENT DOCUMENTS 4,455,675 A 6/1984 Bose et al.
5,638,022 A 6/1997 Eatwell
(Continued)

FOREIGN PATENT DOCUMENTS

EP 2223855 A1 9/2010
GB 2487125 A 7/2012
(Continued)

OTHER PUBLICATIONS

Search Report for British Patent Application No. GB1208152.7 mailed Aug. 15, 2013.
(Continued)

*Primary Examiner* — Simon King
(74) *Attorney, Agent, or Firm* — John W. Branch; Lowe Graham Jones PLLC

(57) ABSTRACT

Embodiments are directed towards enabling headphones to perform active noise cancellation for a particular user. Each separate user may enable individualized noise canceling headphones for one or more noise environments. When the user is wearing the headphones in a quiet environment, a user may employ a computer to initiate determination of a plant model of each ear cup specific to the user. When the user is wearing the headphones in a target noise environment, the user may utilize the computer to initiate determination of operating parameters of a controller for each ear cup of the headphones. The computer may provide the operating parameters of each controller to the headphones. And the operation of each controller may be updated based on the determined operating parameters. The updated headphones may be utilized by the user to provide active noise cancellation.

20 Claims, 17 Drawing Sheets

(51) Int. Cl.
*G10K 11/178* (2006.01)
*H04R 1/10* (2006.01)

(52) U.S. Cl.
CPC *G10K2210/3035* (2013.01); *G10K 2210/3055* (2013.01); *G10K 2210/504* (2013.01); *H04R 1/1083* (2013.01)

(56) References Cited

U.S. PATENT DOCUMENTS

| | | | | |
|---|---|---|---|---|
| 6,418,227 | B1 | 7/2002 | Kuo | |
| 8,447,045 | B1 | 5/2013 | Laroche | |
| 2008/0310645 | A1 | 12/2008 | Itabashi et al. | |
| 2011/0158419 | A1* | 6/2011 | Theverapperuma et al. | 381/71.1 |
| 2013/0083939 | A1* | 4/2013 | Fellers et al. .............. | 381/71.11 |
| 2014/0105412 | A1 | 4/2014 | Alves et al. | |

FOREIGN PATENT DOCUMENTS

| | | | |
|---|---|---|---|
| GB | 2501325 | A | 10/2012 |
| WO | 01/37435 | A2 | 5/2001 |

OTHER PUBLICATIONS

Alves et al., "Convergence Analysis of an Oversampled Subband Adaptive Filtering Structure Using Global Error," Proc. IEEE Int. Conf. on Audio, Speech and Signal Processing (ICASSP), Orlando, FL, Jun. 2000, pp. 468-471.
BlueCore5-Multimedia Flash—Product Data Sheet. 3 pages.
Sony Noise Cancelling Headphones, model MDR-NC500D, Product Manual. 8 pages.
Akhtar. "Hybrid Active noise control system for correlated and uncorrelated noise sources". Proceedings of the 6th International Symposium on Image and signal processing and analysis. pp. 17-21.
Diniz. "Adaptive Filtering: Algorithms and Practical Implementation," Prentice Hall, pp. 376-378.
Elliot, "Signal Processing for Active Control," Academic Press 2001.
Kuo et al., "Active noise control system for headphone applications", Transactions on control systems technology, vol. 14, No. 2, Mar. 2006, pp. 331-335.
Kuo et al., "Active Noise Control Systems, Algorithms and DSP Implementations," John Wiley and Sons, Inc. 1996.
Kuo et al., "Active noise control: A tutorial review", Proceedings of the IEEE, vol. 87, No. 6, Jun. 1999, pp. 943-973.
Morgan, "A delayless subband adaptive filter architecture", IEEE transactions on signal processing, vol. 43, No. 8, Aug. 1995, pp. 1819-1830.
Rafaely, "Feedback control of sound", Ph. D Thesis, University of Southampton Oct. 1997.
Song et al., "A robust hybrid feedback active noise cancellation headset", IEEE transactions on speech and audio processing, vol. 13. No. 4 Jul. 2005, pp. 607-617.
Streeter et al.,"Hybrid Feedforward active noise control", Proceedings of the 2004 American Control Conference, pp. 2876-2881.
Yu et al., "Controller Design for Active Noise Cancellation Headphones using experimental raw data", IEEE/ASME transactions on mechatronics, vol. 6, No. 4, Dec. 2001, pp. 483-490.
Zangi. "A new two-sensor Active noise cancellation algorithm", 1993 IEEE, 0-7803-0946-4/93, pp. 11-351-11-354.
Search Report of Application No. GB1421652.7 mailed on Jun. 1, 2015, 4 pages.

* cited by examiner

USER DESIGNED ACTIVE NOISE CANCELLATION (ANC) CONTROLLER FOR HEADPHONES

CROSS REFERENCE TO RELATED APPLICATIONS

The present application is a Continuation-in-Part of U.S. patent application Ser. No. 13/434,350 filed Mar. 29, 2012, entitled "CONTROLLERS FOR ACTIVE NOISE CONTROL SYSTEMS," the benefit of which is claimed under 35 U.S.C. §120 and 37 C.F.R. §1.78, and which is incorporated herein by reference.

TECHNICAL FIELD

The present invention relates generally to noise cancellation headphones, and more particularly, but not exclusively, to designing headphone controllers for a particular user for a current noise environment.

BACKGROUND

Active noise cancellation (ANC) technology has been developing for many years with a range of headphones incorporating ANC technology (also known as ambient noise reduction and acoustic noise cancelling headphones). These ANC headphones often employ a single fixed controller. Typically, headphone manufactures do extensive research and perform various factory tests and tuning to design the parameters of the fixed controller. Manufacturers can then mass produce headphones that employ the designed fixed controller. However, due to the variability in the physical characteristics from one headphone to another, the physical characteristics of the user's ear, and how users wear the headphones, each headphone may perform differently from user to user and may not provide optimum performance for each user. Some ANC headphones may utilize adaptive systems, but these system are often complex and typically require large amounts of computing resource that are generally not available in a headphone system. Thus, it is with respect to these and other considerations that the invention has been made.

BRIEF DESCRIPTION OF THE DRAWINGS

Non-limiting and non-exhaustive embodiments are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
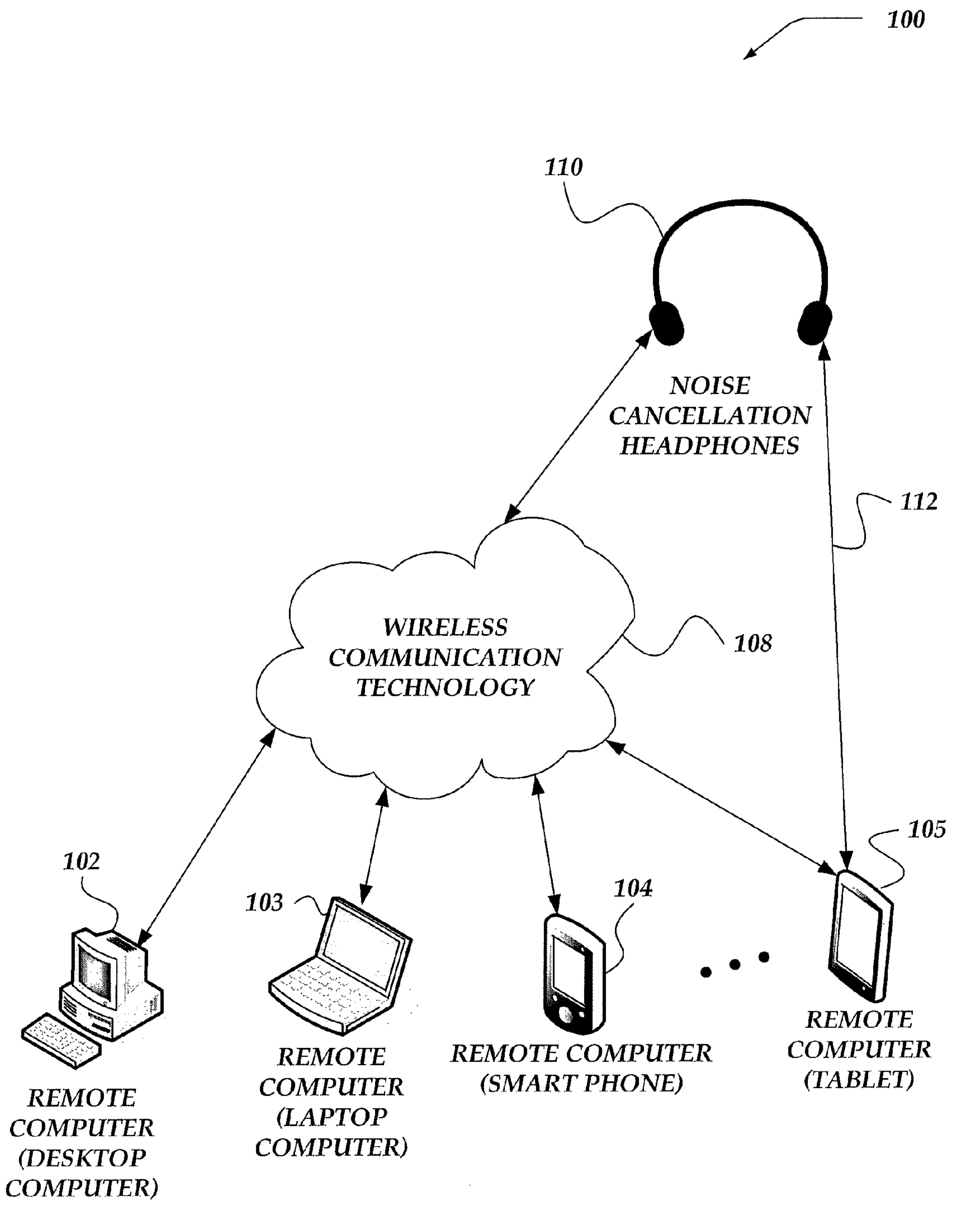
FIG. 1 is a system diagram of an environment in which embodiments of the invention may be implemented.

Various embodiments are described more fully hereinafter with reference to the accompanying drawings, which form a part hereof, and which show, by way of illustration, specific embodiments by which the invention may be practiced. The embodiments may, however, be embodied in many different forms and should not be construed as limited to the embodiments set forth herein; rather, these embodiments are provided so that this disclosure will be thorough and complete, and will fully convey the scope of the embodiments to those skilled in the art. Among other things, the various embodiments may be methods, systems, media, or devices. Accordingly, the various embodiments may be entirely hardware embodiments, entirely software embodiments, or embodiments combining software and hardware aspects. The following detailed description should, therefore, not be limiting.

Throughout the specification and claims, the following terms take the meanings explicitly associated herein, unless the context clearly dictates otherwise. The term "herein" refers to the specification, claims, and drawings associated with the current application. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the term "headphone" or "headphones" refers to a device with one or more ear cups, typically two ear cups, and a headband that is operative to position the ear cups of a user's ears. It should be recognized that the headband may fit over a user's head, behind a user's head, or in some other position to maintain the ear cups over the user's ear. In some other embodiments, each ear cup may include an ear hook or other support structure to maintain a position of the ear cup. In some embodiments, headphones may also be referred to as "noise cancellation headphones."

As used herein, the term "ear cup" refers to a device that fits in or over the ear and converts electric signals into sound waves. Each ear cup may include one or more microphones and one or more speakers. The speakers may provide music, audio signals, or other audible sounds to the user. In some embodiments, each ear cup may be enabled to provide active noise cancellation (ANC) of a noise environment associated with the user wearing the headphones. In various embodiments, the headphones may include other ear cup structures/configurations, such as, but not limited to, earphones, earbuds, loudspeakers, or the like.

As used herein, the term "noise environment" or "environmental noise" refers to ambient noise associated with a user that is wearing the headphones. In some embodiments, the noise environment may include all noise that surround the user and are audible to the user. In other embodiments, the noise environment may include all noise audible to the user except desired sounds produced by the ear cup speaker (e.g., the playing of music). The noise environment may also be referred to as background noise and/or interference other than the desired sound source.

As used herein, the term "controller" or "hardware controller" refers to a device or component that can determine and/or generate noise cancellation signals. Examples of controllers may include, but are not limited to, feedforward controllers, feedback controllers, hybrid feedforward-feedback controllers, or the like. In various embodiments, a controller may have a design or at least one operating parameter that determines the operation of the controller. In some embodiments, the operating parameters of a controller may include and/or employ one or more coefficients to define the transfer function for generating noise cancellation signals. In some embodiments, the controller may be a fixed controller. In various embodiments, the controller may be implemented in hardware, software, or a combination of hardware and software.

As used herein, the term "fixed controller" or "non-adaptive controller" refers to a controller whose design/operating parameters (e.g., coefficients) does not change based on input signals from one or more microphones during operation of the headphones.

As used herein, the term "plant" refers to the relationship between an input signal and an output signal based on physical properties associated with an ear cup positioned over or adjacent to a user's ear. Various components that can make up the plant may include, but are not limited to, physical features of the user (e.g., size and/or shape of the ear, length of the user's hair, whether the user is wearing eye glasses, or the like), the interior shape of the ear cup, the speaker, a microphone internal to the ear cup (which may be utilized to capture residual noise), other circuitry associated with the speaker and/or microphone (e.g., delays in buffers, filtering, analog-to-digital converter characteristics, digital-to-analog converter characteristics, or the like), mechanical characteristics of the headphones (e.g., the pressure of the ear cup on the user's head), or the like, or any combination thereof.

As used herein, the term "plant model" of an ear cup refers to an estimate of the plant for a particular user using a specific ear cup. In various embodiments, each ear cup of the headphones may have a different plant model determined for each of a plurality of different users. In at least one embodiment, as described herein, the plant model of an ear cup may be determined based on a comparison of a reference signal provided to a speaker within the ear cup and an audio signal captured by a microphone within the ear cup.

The following briefly describes embodiments of the invention in order to provide a basic understanding of some aspects of the invention. This brief description is not intended as an extensive overview. It is not intended to identify key or critical elements, or to delineate or otherwise narrow the scope. Its purpose is merely to present some concepts in a simplified form as a prelude to the more detailed description that is presented later.

Briefly stated, various embodiments are directed to enabling headphones to perform active noise cancellation for a particular user. Each of a plurality of users may be enabled to separately configure and/or calibrate each ear cup of a pair of headphones for themselves and for one or more noise environments. When configuring the headphones for a user, a user may wear the headphone in a quiet location with current quiet environment. The user may utilize a smart phone or other remote computer to initiate the process of determining a plant model for each ear cup for that particular user. In some embodiments, the headphones and remote computer may communicate via a wired or wireless communication technology.

In some embodiments, a plant model may be determined for each ear cup for a particular user. The plant model may be based on at least one reference audio signal provided by at least one speaker within each ear cup (e.g., inside the ear cup) and an audio signal captured at the same time by a microphone located within each ear cups (e.g., inside the ear cup). In some embodiments, the plant model for a corresponding ear cup may be determined based on a comparison of the captured signal and the reference signal (which may also be referred to as a sample signal). In at least one of various embodiments, the headphones may provide the captured signal to the remote computer, and the remote computer may determine the plant model.

Once the plant model for each ear cup for a particular user is determined, the user may calibrate each ear cup of the headphones for a particular noise environment. The user may wear the headphones in a location that includes a current target noise environment that the user would like to cancel out. Again, the user may utilize the remote computer to initiate the process of determining at least one operating parameter (also referred to as a design) of a controller for each ear cup of the headphones. In various embodiments, the operating parameters/design may be determined for each controller that corresponds to each ear cup based on at least each ear cup's corresponding plant model and at least one other audio signal from the current noise environment which is captured at the same time by at least one microphone that corresponds to each ear cup (at least one microphone may be internal, external, or both depending on a type of controller employed). Each controller may be a feedback controller, feedforward controller, or a hybrid feedback-feedforward controller. In various embodiments, the headphones may provide the other captured signals to the remote computer, and the remote computer may determine the design of each controller.

In some embodiments, the operating parameters may be determined by employing a microphone located within each ear cup to capture at least one current audio signal of the current noise environment within each ear cup and employing another microphone located external to each ear cup to capture at least one other current audio signal of the current noise environment external to each ear cup. The operating parameters of each controller may be determined based on the plant model of each ear cup and a comparison of at least one captured current audio signal (i.e., an internal current noise environment) and at least one other captured current audio signal (i.e., an external current noise environment) for each ear cup. In some embodiments, determining at least one operating parameter for each controller may include determining at least one coefficient for a non-adaptive mode of operation for each controller, wherein at least one coefficient defines a transfer function employed by each hardware controller to provide the active noise cancellation.

The operation of each controller of each ear cup may be updated based on the determined operating parameters (or design) for each corresponding controller. In at least one of various embodiments, each controller may be updated by storing the operating parameters of each controller in a memory corresponding to each controller and/or ear cup. In various embodiments, once determined, the remote computer may provide the operating parameters to the headphones for storage on a memory of the headphones. Each controller may be updated based on the determined operating parameters. The updated headphones may be utilized by at least the user to provide active noise cancellation of the current noise environment or of another noise environment. In some other embodiments, the operating parameters for each controller may be automatically determined and each controller automatically updated based on a change in the current noise environment.

Although primarily described herein as the remote computer determining the plant model and the operating parameters, embodiments are not so limited. For example, in some embodiments, each ear cup may include sufficient computing power and memory to perform the process of determining a plant model and/or controller operating parameters for a corresponding ear cup. In some embodiments, the headphones may provide the plant model and/or the controller operating parameters to a remote computer. In various embodiments, the remote computer may be utilized to manage user profiles (each user profile may include the plant model for a particular user) and/or noise environment profiles (each noise environment profile may include controller operating parameters for each ear cup for one or more noise environments for each user profile). As described herein, the remote computer may be utilized to switch between different user profiles and/or different noise environment profiles. However, embodiments are not so limited. For example, in some embodiments, the headphones may include an additional interface (e.g., one or more buttons) to enable a user to switch between one or more controller operating parameters for one or more users (e.g., different plant models).

Illustrative Operating Environment

FIG. 1 shows components of one embodiment of an environment in which various embodiments of the invention may be practiced. Not all of the components may be required to practice the various embodiments, and variations in the arrangement and type of the components may be made without departing from the spirit or scope of the invention. As shown, system 100 of FIG. 1 may include network noise cancellation headphones 110, remote computers 102-105, and wireless communication technology 108.

At least one embodiment of remote computers 102-105 is described in more detail below in conjunction with computer 200 of FIG. 2. Briefly, in some embodiments, remote computers 102-105 may be configured to communicate with noise cancellation headphones 110 to determine a plant of each ear cup of the headphones specific to each user and to configure a controller design for each ear cup for a current noise environment, as described herein. In various embodiments, remote computers 102-105 may be a separate and/or remote from headphones 110.

In some other embodiments, at least some of remote computers 102-105 may operate over a wired and/or wireless network to communicate with noise cancellation headphones 110 or other computing devices. Generally, remote computers 102-105 may include computing devices capable of communicating over a network to send and/or receive information, perform various online and/or offline activities, or the like. It should be recognized that embodiments described herein are not constrained by the number or type of remote computers employed, and more or fewer remote computers—and/or types of computing devices—than what is illustrated in FIG. 1 may be employed. In some embodiments, remote computers may also be referred to as client computers.

Devices that may operate as remote computers 102-105 may include various computing devices that typically connect to a network or other computing device using a wired and/or wireless communications medium. Remote computers may include portable and/or non-portable computers. Examples of remote computers 102-105 may include, but are not limited to, desktop computers (e.g., remote computer 102), personal computers, multiprocessor systems, microprocessor-based or programmable electronic devices, network PCs, laptop computers (e.g., remote computer 103), smart phones (e.g., remote computer 104), tablet computers (e.g., remote computer 105), cellular telephones, display pagers, radio frequency (RF) devices, infrared (IR) devices, Personal Digital Assistants (PDAs), handheld computers, wearable computing devices, entertainment/home media systems (e.g., televisions, gaming consoles, audio equipment, or the like), household devices (e.g., thermostats, refrigerators, home security systems, or the like), multimedia navigation systems, automotive communications and entertainment systems, integrated devices combining functionality of one or more of the preceding devices, or the like. As such, remote computers 102-105 may include computers with a wide range of capabilities and features.

Remote computers 102-105 may access and/or employ various computing applications to enable users of remote computers to perform various online and/or offline activities. Such activities may include, but are not limited to, calibrating/configuring headphones 110, generating documents, gathering/monitoring data, capturing/manipulating images, managing media, managing financial information, playing games, managing personal information, browsing the Internet, or the like. In some embodiments, remote computers 102-105 may be enabled to connect to a network through a browser, or other web-based application.

Remote computers 102-105 may further be configured to provide information that identifies the remote computer. Such identifying information may include, but is not limited to, a type, capability, configuration, name, or the like, of the remote computer. In at least one embodiment, a remote computer may uniquely identify itself through any of a variety of mechanisms, such as an Internet Protocol (IP) address, phone number, Mobile Identification Number (MIN), media access control (MAC) address, electronic serial number (ESN), or other device identifier.

At least one embodiment of noise cancellation headphones 110 is described in more detail below in conjunction with headphones 300 of FIG. 3. Briefly, in some embodiments, noise cancellation headphones 110 may be configured to communicate with one or more of remote computers 102-105 to determine a plant of each ear cup of the headphones specific to each user and to configure a controller design (e.g., determine one or more operating parameters that define an operation of a controller) for each ear cup for a current noise environment, as described herein.

Remote computers 102-105 may communicate with noise cancellation headphones 110 via wired technology 112 and/or wireless communication technology 108. In various embodiments, wired technology 112 may include a typical headphone cable with a jack for connecting to an audio input/output port on remote computers 102-105.

Wireless communication technology 108 may include virtually any wireless technology for communicating with a remote device, such as, but not limited to Bluetooth, Wi-Fi, or the like. In some embodiments, wireless communication technology 108 may be a network configured to couple network computers with other computing devices, including remote computers 102-105, noise cancellation headphones 110, or the like. In some other embodiments, wireless communication technology 108 may enable remote computers 102-105 to communicate with other computing devices, such as, but not limited to, other remote devices, various client devices, server devices, or the like. In various embodiments, information communicated between devices may include various kinds of information, including, but not limited to, processor-readable instructions, client requests, server responses, program modules, applications, raw data, control data, system information (e.g., log files), video data, voice data, image data, text data, structured/unstructured data, or the like. In some embodiments, this information may be communicated between devices using one or more technologies and/or network protocols described herein.

In some embodiments, such a network may include various wired networks, wireless networks, or any combination thereof. In various embodiments, the network may be enabled to employ various forms of communication technology, topology, computer-readable media, or the like, for communicating information from one electronic device to another. For example, the network can include—in addition to the Internet—LANs, WANs, Personal Area Networks (PANs), Campus Area Networks (CANs), Metropolitan Area Networks (MANs), direct communication connections (such as through a universal serial bus (USB) port), or the like, or any combination thereof.

In various embodiments, communication links within and/or between networks may include, but are not limited to, twisted wire pair, optical fibers, open air lasers, coaxial cable, plain old telephone service (POTS), wave guides, acoustics, full or fractional dedicated digital lines (such as T1, T2, T3, or T4), E-carriers, Integrated Services Digital Networks (ISDNs), Digital Subscriber Lines (DSLs), wireless links (including satellite links), or other links and/or carrier mechanisms known to those skilled in the art. Moreover, communication links may further employ any of a variety of digital signaling technologies, including without limit, for example, DS-0, DS-1, DS-2, DS-3, DS-4, OC-3, OC-12, OC-48, or the like. In some embodiments, a router (or other intermediate network device) may act as a link between various networks—including those based on different architectures and/or protocols—to enable information to be transferred from one network to another. In other embodiments, remote computers and/or other related electronic devices could be connected to a network via a modem and temporary telephone link. In essence, the network may include any communication technology by which information may travel between computing devices.

The network may, in some embodiments, include various wireless networks, which may be configured to couple various portable network devices, remote computers, wired networks, other wireless networks, or the like. Wireless networks may include any of a variety of sub-networks that may further overlay stand-alone ad-hoc networks, or the like, to provide an infrastructure-oriented connection for at least remote computers 103-105. Such sub-networks may include mesh networks, Wireless LAN (WLAN) networks, cellular networks, or the like. In at least one of the various embodiments, the system may include more than one wireless network.

The network may employ a plurality of wired and/or wireless communication protocols and/or technologies. Examples of various generations (e.g., third (3G), fourth (4G), or fifth (5G)) of communication protocols and/or technologies that may be employed by the network may include, but are not limited to, Global System for Mobile communication (GSM), General Packet Radio Services (GPRS), Enhanced Data GSM Environment (EDGE), Code Division Multiple Access (CDMA), Wideband Code Division Multiple Access (W-CDMA), Code Division Multiple Access 2000 (CDMA2000), High Speed Downlink Packet Access (HSDPA), Long Term Evolution (LTE), Universal Mobile Telecommunications System (UMTS), Evolution-Data Optimized (Ev-DO), Worldwide Interoperability for Microwave Access (WiMax), time division multiple access (TDMA), Orthogonal frequency-division multiplexing (OFDM), ultra wide band (UWB), Wireless Application Protocol (WAP), user datagram protocol (UDP), transmission control protocol/Internet protocol (TCP/IP), any portion of the Open Systems Interconnection (OSI) model protocols, session initiated protocol/real-time transport protocol (SIP/RTP), short message service (SMS), multimedia messaging service (MMS), or any of a variety of other communication protocols and/or technologies. In essence, the network may include communication technologies by which information may travel between remote computers 102-105, noise cancellation headphones 110, other computing devices not illustrated, other networks, or the like.

In various embodiments, at least a portion of the network may be arranged as an autonomous system of nodes, links, paths, terminals, gateways, routers, switches, firewalls, load balancers, forwarders, repeaters, optical-electrical converters, or the like, which may be connected by various communication links. These autonomous systems may be configured to self organize based on current operating conditions and/or rule-based policies, such that the network topology of the network may be modified.

Illustrative Computer

Figure 2:
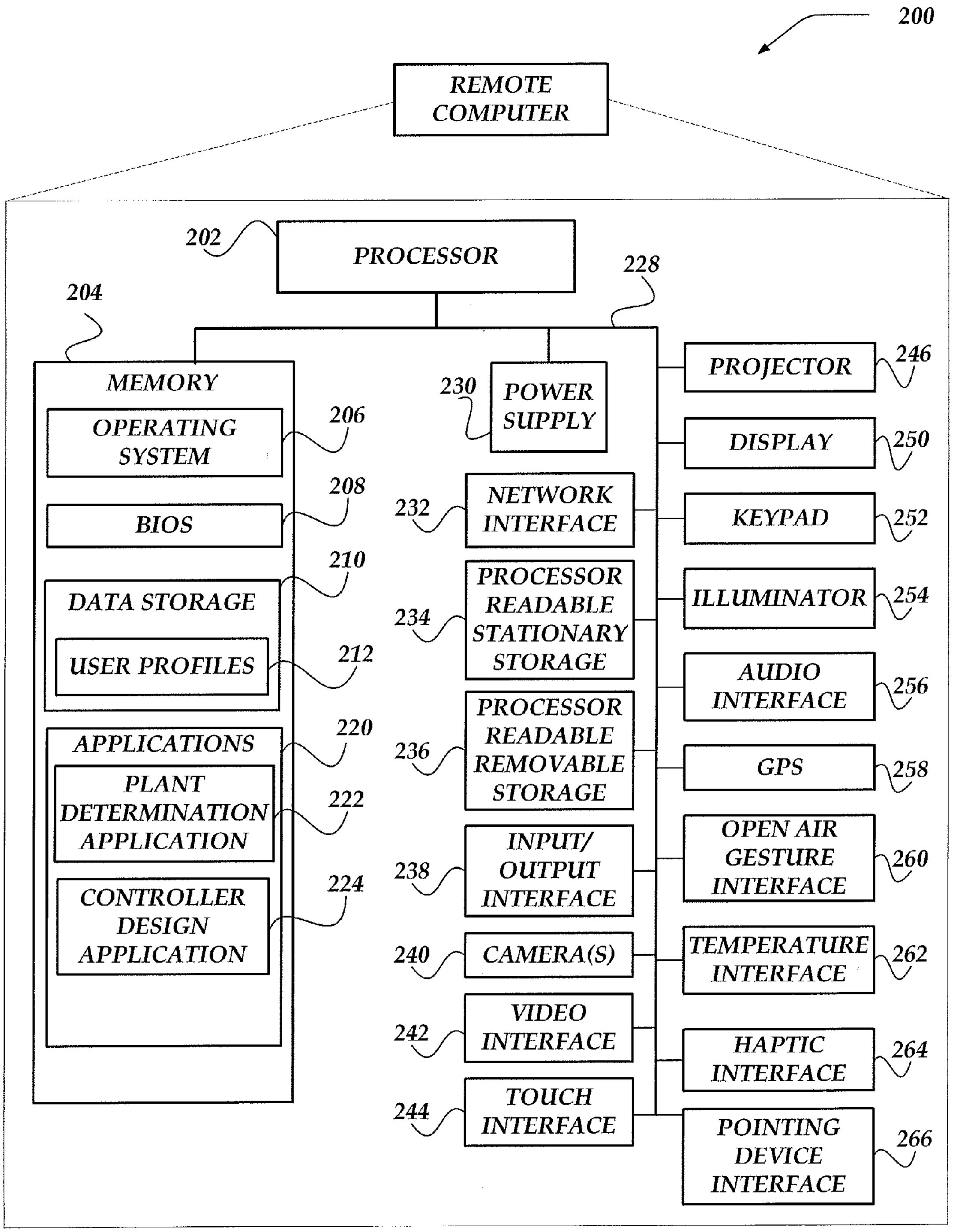
FIG. 2 shows an embodiment of a computer that may be included in a system such as that shown in FIG. 1.

FIG. 2 shows one embodiment of remote computer 200 that may include many more or less components than those shown. Remote computer 200 may represent, for example, at least one embodiment of remote computers 102-105 shown in FIG. 1.

Remote computer 200 may include processor 202 in communication with memory 204 via bus 228. Remote computer 200 may also include power supply 230, network interface 232, audio interface 256, display 250, keypad 252, illuminator 254, video interface 242, input/output interface 238, haptic interface 264, global positioning systems (GPS) receiver 258, open air gesture interface 260, temperature interface 262, camera(s) 240, projector 246, pointing device interface 266, processor-readable stationary storage device 234, and processor-readable removable storage device 236. Remote computer 200 may optionally communicate with a base station (not shown), or directly with another computer. And in one embodiment, although not shown, a gyroscope may be employed within remote computer 200 to measuring and/or maintaining an orientation of remote computer 200.

Power supply 230 may provide power to remote computer 200. A rechargeable or non-rechargeable battery may be used to provide power. The power may also be provided by an external power source, such as an AC adapter or a powered docking cradle that supplements and/or recharges the battery.

Network interface 232 includes circuitry for coupling remote computer 200 to one or more networks, and is constructed for use with one or more communication protocols and technologies including, but not limited to, protocols and technologies that implement any portion of the OSI model, GSM, CDMA, time division multiple access (TDMA), UDP, TCP/IP, SMS, MMS, GPRS, WAP, UWB, WiMax, SIP/RTP, GPRS, EDGE, WCDMA, LTE, UMTS, OFDM, CDMA2000, EV-DO, HSDPA, or any of a variety of other wireless communication protocols. Network interface 232 is sometimes known as a transceiver, transceiving device, or network interface card (NIC). In some embodiments, network interface 232 may enable remote computer 200 to communicate with headphones 300 of FIG. 3.

Audio interface 256 may be arranged to produce and receive audio signals such as the sound of a human voice. For example, audio interface 256 may be coupled to a speaker and microphone (not shown) to enable telecommunication with others and/or generate an audio acknowledgement for some action. A microphone in audio interface 256 can also be used for input to or control of remote computer 200, e.g., using voice recognition, detecting touch based on sound, and the like. In other embodiments this microphone may be utilized to detect changes in the noise environment, which if detected may initialize automatic determination of new controller designs for ear cup controllers and automatically updating the headphones with the new controller designs for the changed noise environment.

Display 250 may be a liquid crystal display (LCD), gas plasma, electronic ink, light emitting diode (LED), Organic LED (OLED) or any other type of light reflective or light transmissive display that can be used with a computer. Display 250 may also include a touch interface 244 arranged to receive input from an object such as a stylus or a digit from a human hand, and may use resistive, capacitive, surface acoustic wave (SAW), infrared, radar, or other technologies to sense touch and/or gestures.

Projector 246 may be a remote handheld projector or an integrated projector that is capable of projecting an image on a remote wall or any other reflective object such as a remote screen.

Video interface 242 may be arranged to capture video images, such as a still photo, a video segment, an infrared video, or the like. For example, video interface 242 may be coupled to a digital video camera, a web-camera, or the like. Video interface 242 may comprise a lens, an image sensor, and other electronics. Image sensors may include a complementary metal-oxide-semiconductor (CMOS) integrated circuit, charge-coupled device (CCD), or any other integrated circuit for sensing light.

Keypad 252 may comprise any input device arranged to receive input from a user. For example, keypad 252 may include a push button numeric dial, or a keyboard. Keypad 252 may also include command buttons that are associated with selecting and sending images.

Illuminator 254 may provide a status indication and/or provide light. Illuminator 254 may remain active for specific periods of time or in response to events. For example, when illuminator 254 is active, it may backlight the buttons on keypad 252 and stay on while the mobile computer is powered. Also, illuminator 254 may backlight these buttons in various patterns when particular actions are performed, such as dialing another mobile computer. Illuminator 254 may also cause light sources positioned within a transparent or translucent case of the mobile computer to illuminate in response to actions.

Remote computer 200 may also comprise input/output interface 238 for communicating with external peripheral devices or other computers such as other mobile computers and network computers. The peripheral devices may include headphones (e.g., headphones 300 of FIG. 3), display screen glasses, remote speaker system, remote speaker and microphone system, and the like. Input/output interface 238 can utilize one or more technologies, such as Universal Serial Bus (USB), Infrared, Wi-Fi, WiMax, Bluetooth™, wired technologies, or the like.

Haptic interface 264 may be arranged to provide tactile feedback to a user of a mobile computer. For example, the haptic interface 264 may be employed to vibrate remote computer 200 in a particular way when another user of a computer is calling. Temperature interface 262 may be used to provide a temperature measurement input and/or a temperature changing output to a user of remote computer 200. Open air gesture interface 260 may sense physical gestures of a user of remote computer 200, for example, by using single or stereo video cameras, radar, a gyroscopic sensor inside a computer held or worn by the user, or the like. Camera 240 may be used to track physical eye movements of a user of remote computer 200.

GPS transceiver 258 can determine the physical coordinates of remote computer 200 on the surface of the Earth, which typically outputs a location as latitude and longitude values. GPS transceiver 258 can also employ other geo-positioning mechanisms, including, but not limited to, triangulation, assisted GPS (AGPS), Enhanced Observed Time Difference (E-OTD), Cell Identifier (CI), Service Area Identifier (SAI), Enhanced Timing Advance (ETA), Base Station Subsystem (BSS), or the like, to further determine the physical location of remote computer 200 on the surface of the Earth. It is understood that under different conditions, GPS transceiver 258 can determine a physical location for remote computer 200. In at least one embodiment, however, remote computer 200 may, through other components, provide other information that may be employed to determine a physical location of the mobile computer, including for example, a Media Access Control (MAC) address, IP address, and the like.

Human interface components can be peripheral devices that are physically separate from remote computer 200, allowing for remote input and/or output to remote computer 200. For example, information routed as described here through human interface components such as display 250 or keyboard 252 can instead be routed through network interface 232 to appropriate human interface components located remotely. Examples of human interface peripheral components that may be remote include, but are not limited to, audio devices, pointing devices, keypads, displays, cameras, projectors, and the like. These peripheral components may communicate over a Pico Network such as Bluetooth™, Zigbee™ and the like. One non-limiting example of a mobile computer with such peripheral human interface components is a wearable computer, which might include a remote pico projector along with one or more cameras that remotely communicate with a separately located mobile computer to sense a user's gestures toward portions of an image projected by the pico projector onto a reflected surface such as a wall or the user's hand.

A remote computer may include a browser application that is configured to receive and to send web pages, web-based messages, graphics, text, multimedia, and the like. The mobile computer's browser application may employ virtually any programming language, including a wireless application protocol messages (WAP), and the like. In at least one embodiment, the browser application is enabled to employ Handheld Device Markup Language (HDML), Wireless Markup Language (WML), WMLScript, JavaScript, Standard Generalized Markup Language (SGML), HyperText Markup Language (HTML), eXtensible Markup Language (XML), HTML5, and the like.

Memory 204 may include RAM, ROM, and/or other types of memory. Memory 204 illustrates an example of computer-readable storage media (devices) for storage of information such as computer-readable instructions, data structures, program modules or other data. Memory 204 may store BIOS 208 for controlling low-level operation of remote computer 200. The memory may also store operating system 206 for controlling the operation of remote computer 200. It will be appreciated that this component may include a general-purpose operating system such as a version of UNIX, or LINUX™, or a specialized mobile computer communication operating system such as Windows Phone™, or the Symbian® operating system. The operating system may include, or interface with a Java virtual machine module that enables control of hardware components and/or operating system operations via Java application programs.

Memory 204 may further include one or more data storage 210, which can be utilized by remote computer 200 to store, among other things, applications 220 and/or other data. For example, data storage 210 may also be employed to store information that describes various capabilities of remote computer 200. The information may then be provided to another device or computer based on any of a variety of events, including being sent as part of a header during a communication, sent upon request, or the like. Data storage 210 may also be employed to store social networking information including address books, buddy lists, aliases, user profile information, or the like. Data storage 210 may further include program code, data, algorithms, and the like, for use by a processor, such as processor 202 to execute and perform actions. In one embodiment, at least some of data storage 210 might also be stored on another component of remote computer 200, including, but not limited to, non-transitory processor-readable removable storage device 236, processor-readable stationary storage device 234, or even external to the mobile computer.

In some embodiments, data storage 210 may store user profiles 212. User profiles 212 may include one or more profiles for each of a plurality of users. Each profile may include a plant model of each ear cup of the headphones for a corresponding user (such as may be determined by employing embodiments of process 600 of FIG. 6). In various embodiments, each profile may include one or more noise environment profiles. Each noise environment profile may include a controller design (e.g., controller coefficients) for each controller of each ear cup of the headphones (such as may be determined by employing embodiments of process 700 of FIG. 7 or process 800 of FIG. 8).

Applications 220 may include computer executable instructions which, when executed by remote computer 200, transmit, receive, and/or otherwise process instructions and data. Applications 220 may include, for example, plant determination application 222, and controller design application 224. It should be understood that the functionality of plant determination application 222 and controller design application 224 may be employed as a separate applications or as a single application.

Plant determination application 222 may be configured to determine a plant of an ear cup specific to a user, as described herein. In any event, plant determination application 222 may be configured to employ various embodiments, combinations of embodiments, processes, or parts of processes, as described herein.

Controller design application 224 may be configured to determine a design of at least one controller of an ear cup specific to a user for a specific noise environment, as described herein. In any event, controller design application 224 may be configured to employ various embodiments, combinations of embodiments, processes, or parts of processes, as described herein. Although illustrated separately, plant determination application 222 and controller design application 224 may be separate applications or a single application, and may enable a user to access information stored in user profiles 212. In at least one of various embodiments, a mobile application (or app) may be configured to include the functionality of plant determination application 222, controller design application 224, and enable access to user profiles 212.

Other examples of application programs include calendars, search programs, email client applications, IM applications, SMS applications, Voice Over Internet Protocol (VOIP) applications, contact managers, task managers, transcoders, database programs, word processing programs, security applications, spreadsheet programs, games, search programs, and so forth.

Illustrative Headphones

Figure 3:
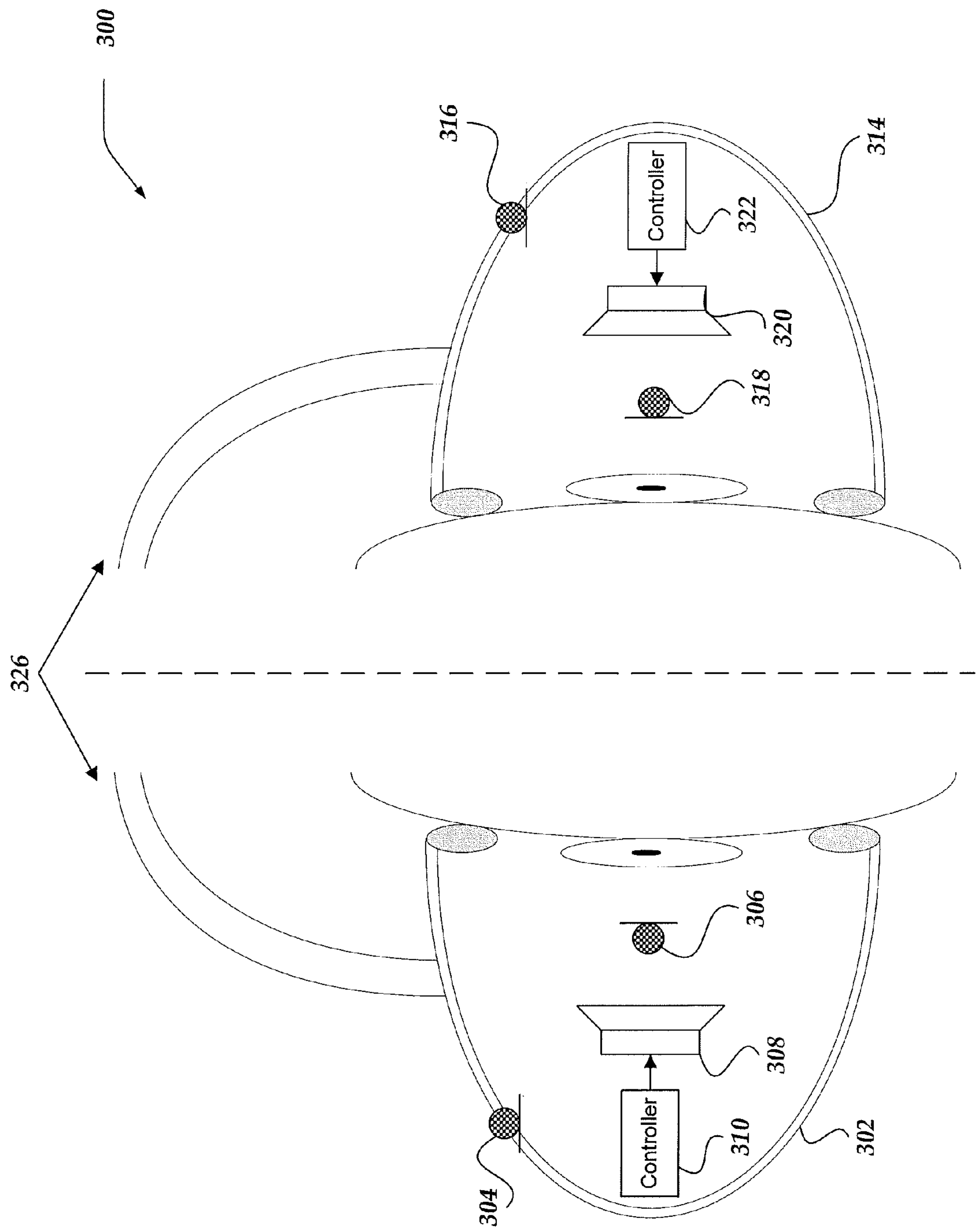
FIG. 3 shows an embodiment of active noise canceling headphones that may be included in a system such as that shown in FIG. 1.

FIG. 3 shows an embodiment of active noise canceling headphones that may be including in a system such as that shown in FIG. 1, e.g., headphones 300 may be an embodiment of noise cancellation headphones 110.

Headphones 300 may include headband 326 and one or more ear cups, such as ear cup 302 and ear cup 314. Headband 326 may be operative to hold the ear cups over and/or adjacent to the ears of a user. In some embodiments, ear cups 302 and 314 may be operative to provide active noise cancellation of environmental noise. Each ear cup may be configured to cover a user's left ear, right ear, or universal for covering either ear. For ease of illustration and description, the ear cups will be described without reference to left ear or right ear, but noting that the embodiments described herein can be employed for such a distinction.

Ear cup 302 may include external microphone 304, internal microphone 306, speaker 308, and controller 310. Speaker 308 may be operative to produce sound, such as music or other audible signals. In some embodiments, speaker 308 may produce sounds that canceling or minimize environmental noise. In at least one of various embodiments, ear cup 302 may include multiple speakers.

Controller 310 may be operative to generate and/or otherwise determine noise cancellation signals based on inputs from external microphone 304, internal microphone 306, or both. Controller 310 may be a feedforward controller, a feedback controller, or a hybrid feedforward-feedback controller. These types of controller are well known in the art, but briefly, a feedforward controller can utilize a signal generated from external microphone 304 to generate the noise canceling signal. A feedback controller can utilize a signal generated from internal microphone 306 to generate the noise canceling signal. And a hybrid feedforward-feedback controller can utilize the signals from both external microphone 304 and internal microphone 306 to generate the noise canceling signal. In various embodiments, controller 310 may be implemented in hardware and referred to as a hardware controller. In other embodiments, controller 310 may be implemented in software or a combination of hardware and software.

In some embodiments, controller 310 may be a fixed controller or non-adaptive controller, in that the controller (or design of the controller, e.g., controller coefficients) itself does not change based on the inputs from the microphones. In various embodiments, controller 310 may be a discrete digital controller or an analog controller. In at least one of various embodiments, controller 310 may be updated with one or more coefficients to enable a non-adaptive mode of operation by the controller.

As described herein, controller 310 may be enabled to access one or more coefficients (e.g., operating parameters) that define a transfer function for the generation of the noise cancellation signals. Controller 310 may be implemented by a digital signal processor, a microcontroller, other hardware chips/circuits, or the like. In some embodiments, controller 310 may be part of a hardware chip that provides signals to speaker 308, receives signals from microphones 304 and 306, provides noise cancellation functionality, and communicates with a remote computing device, as described herein. In various embodiments, one or more chips may be employed to perform various aspects/functions of embodiments as described herein.

In at least one of various embodiments, controller 310 may include and/or be associated with a memory device (not illustrated), such as but not limited to, on-chip memory (e.g., chip registers, RAM, or the like), off-chip RAM, or the like. This memory device may store the coefficients utilized by controller 310. As described herein, these coefficients may be changed and/or otherwise overwritten within the memory for different users, different noise environments, or the like.

External microphone 304 may be operative to capture noise signals that are external to ear cup 302 (e.g., external noise environment). In some embodiments, external microphone 304 may be insulated and/or shielded to minimize noise or other audio signals coming from inside ear cup 302 (e.g., sound produced by speaker 308).

Internal microphone 306 may be operative to capture noise signals that are internal to ear cup 302 (e.g., internal noise environment). In some embodiments, internal microphone 306 may be positioned approximate to speaker 308, such as between speaker 308 and an opening of the ear cup towards the user's ear.

In various embodiments, ear cup 314 may include similar components and provide similar functionality as ear cup 302. For example, external microphone 316 and internal microphone 318 may be embodiments of external microphone 304 and internal microphone 306, respectively, but they capture noise with respect to ear cup 314 rather than ear cup 302. Similarly, controller 322 may be an embodiment of controller 310 and speaker 320 may be an embodiment of speaker 308.

It should be understood that headphones 300 may include additional components not illustrated. For example, in various embodiments, headphones 300 may include an interface device for communicating with a remote computing device, such as remote computer 200 of FIG. 2. In some embodiments, the headphones may include a single interface device for communicating with the remote computing device. In other embodiments, each ear cup may include a separate interface device. An interface device may include a wired connection with the remote computing device and/or a wireless interface (e.g., Bluetooth).

In at least one of various embodiments, the interface device may include a wire that can directly connect to the computing device to send and/or receive signals (e.g., analog or digital signals) to and from the computing device. An example of such a wire may include a typical headphone cable with a jack for connecting to a MP3 player, mobile phone, tablet computer, or the like. In some other embodiments, the interface device may include a wireless communication interface for sending and/or receiving signals to the computing device over a wireless protocol. Such wireless protocols may include, but are not limited to, Bluetooth, Wi-Fi, or the like. In various embodiments, headphones 300 may be enabled to provide signals captured from external microphone 304, internal microphone 306, external microphone 316, and/or internal microphone 318 to the remote computing device (e.g., a mobile computer) through the headphone interface device.

Example System Diagram

Figure 4A:
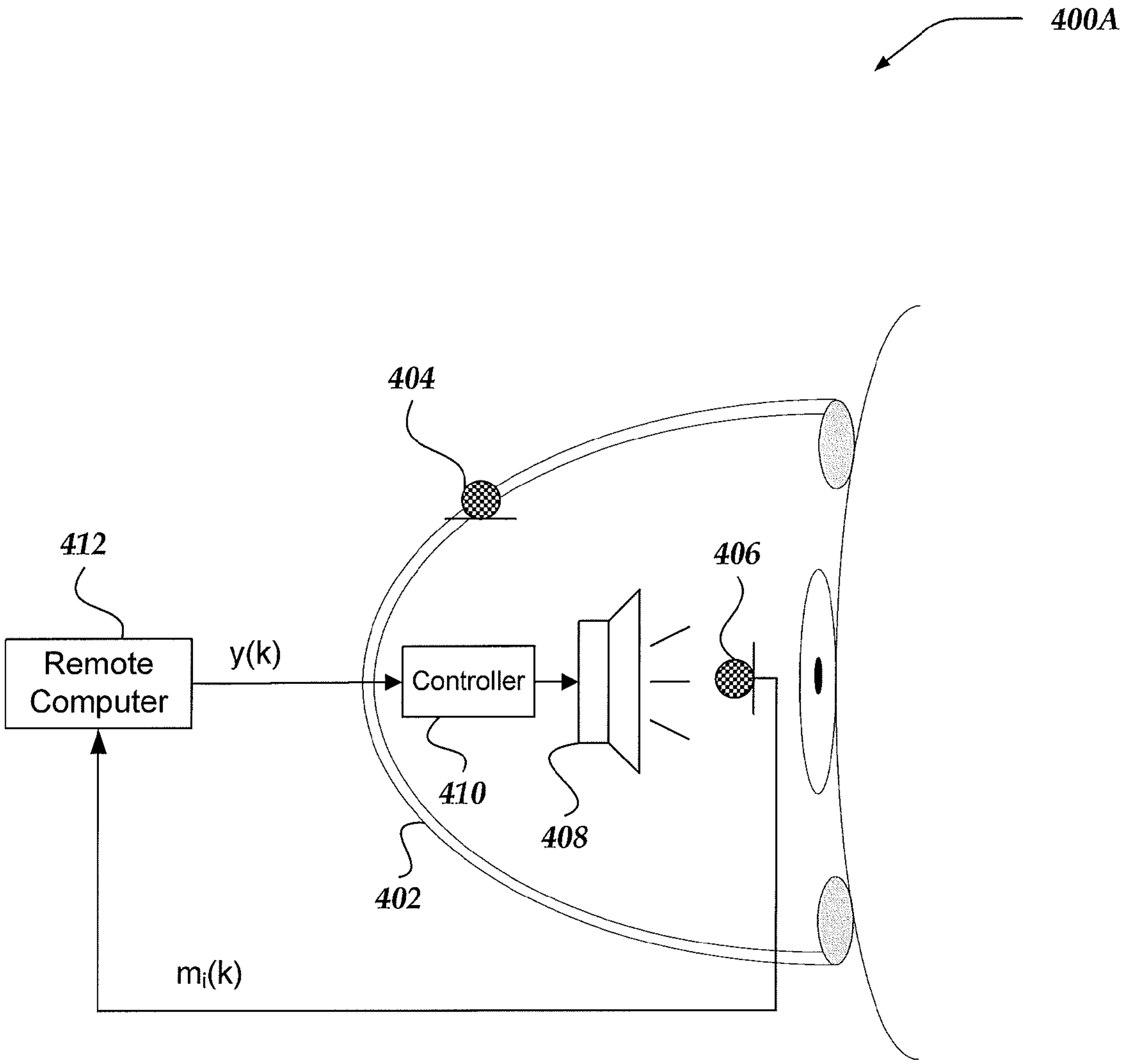
FIGS. 4A-4C illustrate block diagrams of a system for updating a controller of a headphones' ear cup.
Figure 4B:
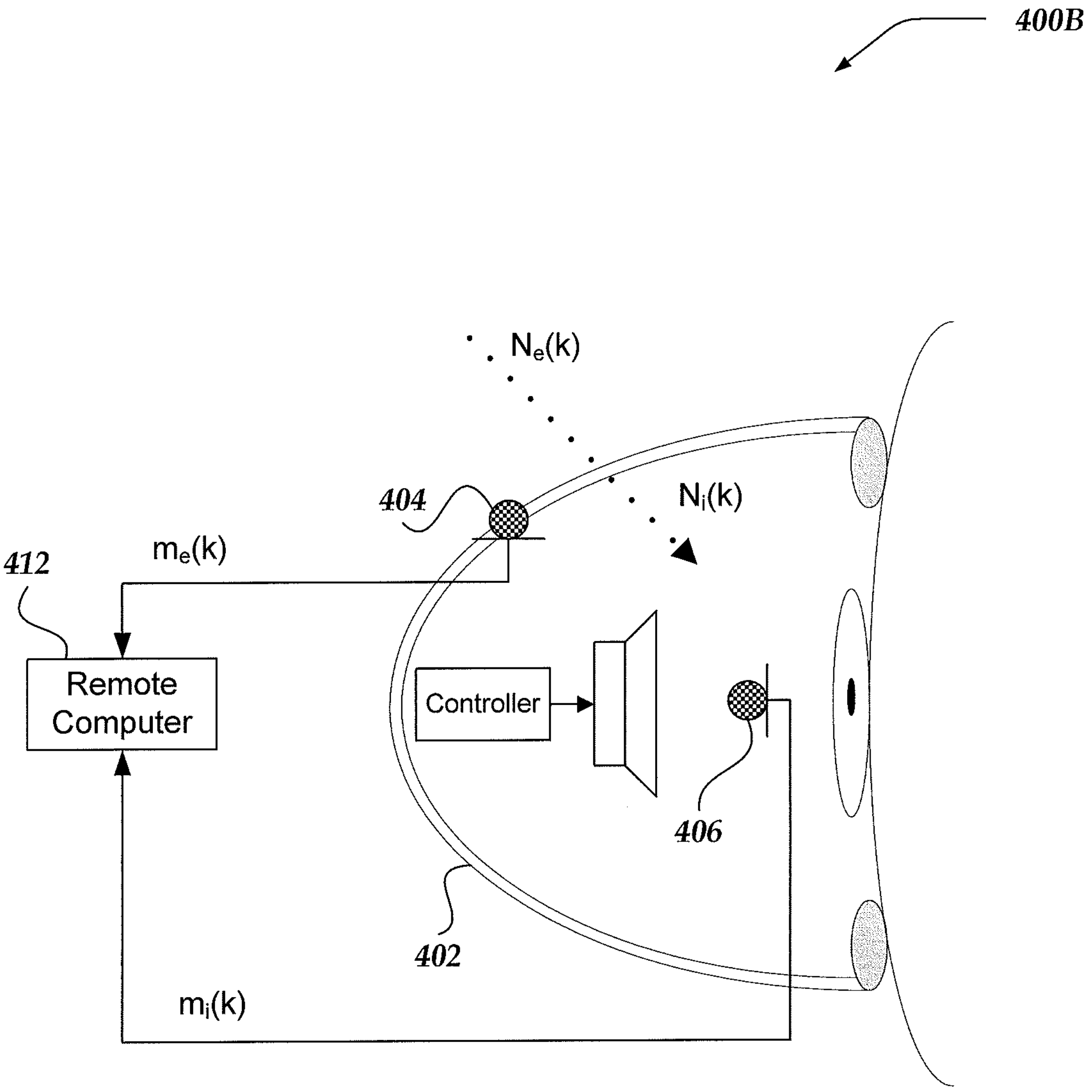
Figure 4C:
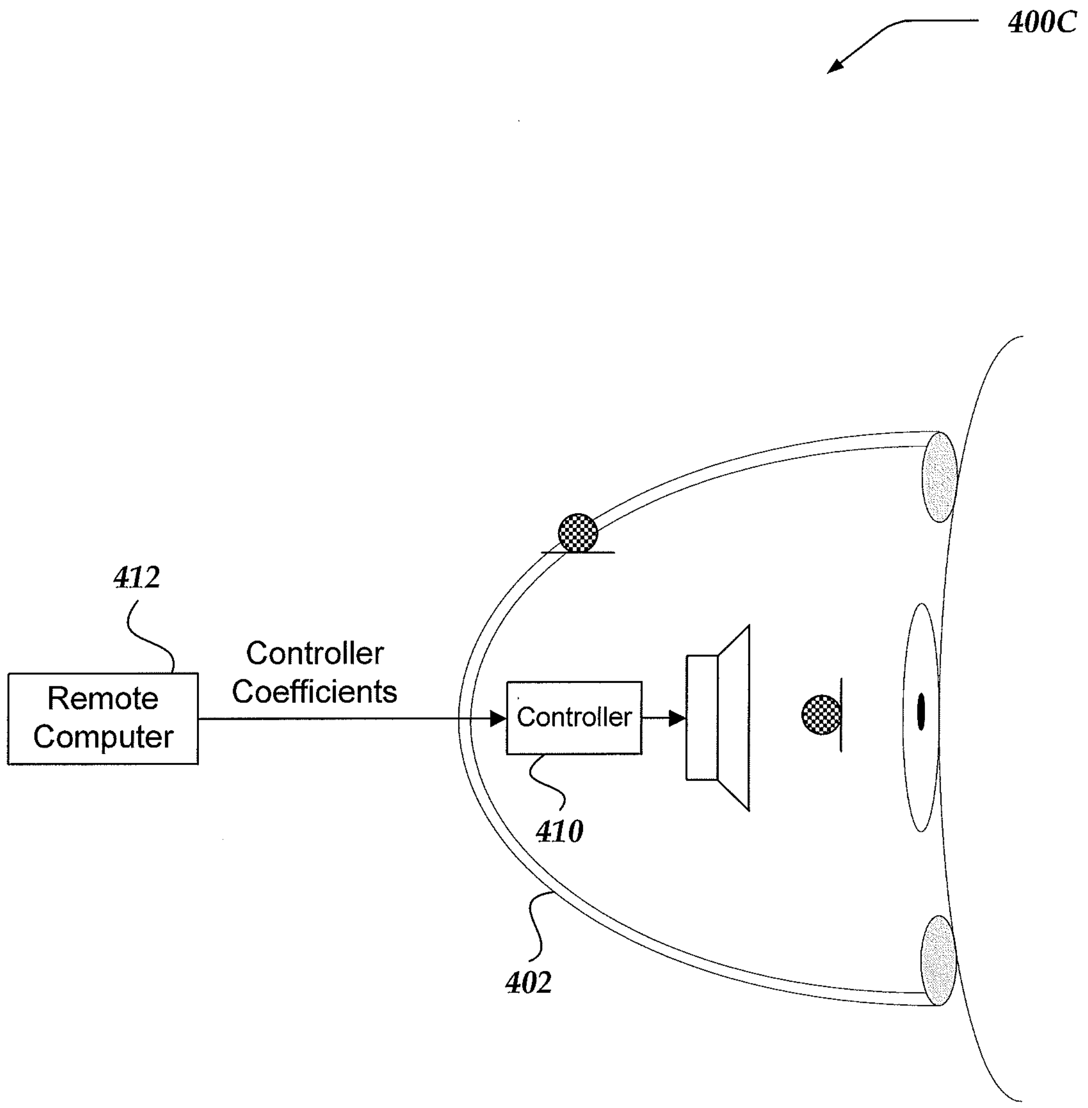

FIGS. 4A-4C illustrate block diagrams of a system for updating a controller of a headphones' ear cup.

FIG. 4A illustrates a block diagram of system for determining a plant model of a headphones' ear cup for a particular user. System 400A may include ear cup 402 and remote computer 412. It should be recognized that a similar system may be employed for another ear cup of a same pair of headphones using a same remote computer.

In some embodiments, remote computer 412 may be an embodiment of remote computer 200 of FIG. 2, which may be remote to the headphones. In various embodiments, ear cup 402 may be an embodiment of ear cup 302 of FIG. 3. Ear cup 402 may include external microphone 404, internal microphone 406, speaker 408, and controller 410, which may be embodiments of external microphone 304 of FIG. 3, internal microphone 306 of FIG. 3, speaker 308 of FIG. 3, and controller 310 of FIG. 3, respectively.

A user may be instructed to wear the headphones. The user may wear the headphones on their head as he or she so desires. Since users wear headphones in different fashions (e.g., above the ears, behind the ear, or the like) and have different physical features (e.g., size of ears, length of hair, wear glasses, or the like), the plant model of the ear cup can be determined for each separate user.

While the user is wearing the headphones and in a current quiet environment (e.g., a room with very little to no ambient noise), remote computer 412 can be instructed to initiate the process of determining the plant model. In some embodiments, the plant model may be determined while the user is wearing the headphones in a noisy or non-quiet environment. In at least one such embodiment, an initial, default, or current controller configuration may be utilized to cancel or reduce the noisy environment. In at least one of various embodiments, the user may utilize a mobile application or other application/program to begin the plant model determination process.

Figure 10A:
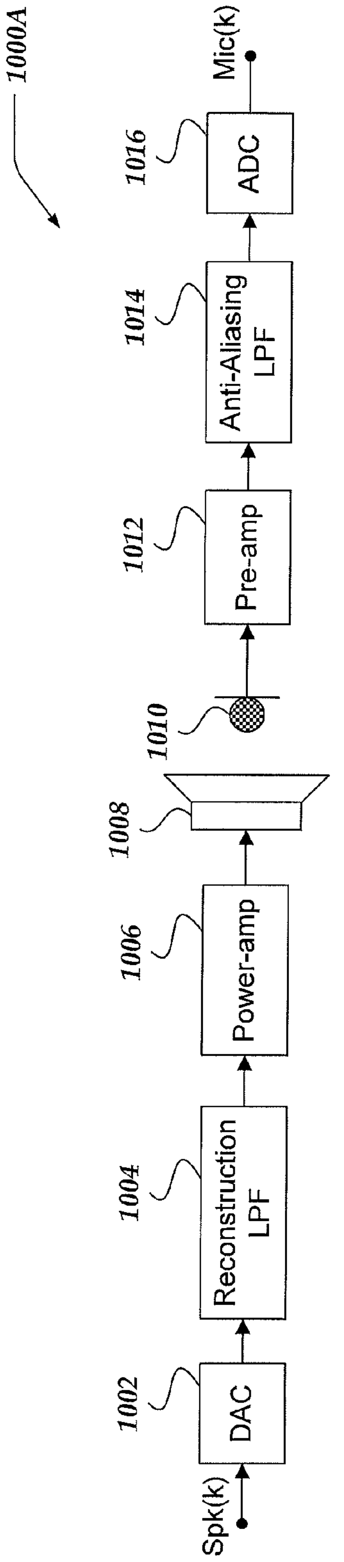
FIGS. 10A-10B illustrate block diagrams of embodiments of a system for determining a plant model for a headphone ear cup.

Once initiated, remote computer 412 may provide signal y(k) to speaker 408. In some embodiments, signal y(k) may be referred to as a reference signal or a sample signal. In some embodiments, signal y(k) may be processed prior to being output by speaker 408, such as shown in FIG. 10A (where signal y(k) in FIG. 4A is equal to signal Spk(k) in FIG. 10A). In some embodiments, signal y(k) may pass through controller 410 to speaker 408 without adding noise canceling signals, so that the sound produced by speaker 408 is an audible representation of signal y(k). Although various embodiments described herein are in the digital domain (which are represented in terms of time k), embodiments are not so limited. In at least one of various embodiments, signal y(k) output by speaker 408 may be referred to as a reference audio signal.

Internal microphone 406 may capture signal $m_i(k)$ while signal y(k) is being played by speaker 408 at the same time. In some embodiments, the signal captured by internal microphone 406 may be processed to obtain signal $m_i(k)$, such as shown in FIG. 10A (where signal $m_i(k)$ in FIG. 4A is equal to signal Mic(k) in FIG. 10A). The headphones may provide signal $m_i(k)$ to remote computer 412 (e.g., using a wire or wireless communication technology). In some embodiments, signal $m_i(k)$ may be recorded and/or otherwise stored in a memory (not illustrated) of ear cup 402 or the headphones prior to sending to remote computer 412.

Remote computer 412 may utilize signals y(k) and $m_i(k)$ to determine the plant model for ear cup 402 for the user wearing the headphones. Remote computer 412 may employ embodiments described in conjunction with FIG. 10B to determine the plant model of ear cup 402 based on signals y(k) and $m_i(k)$, where signal $m_i(k)$ in FIG. 4A is equal to signal Mic(k) in FIG. 10B and where signal y(k) in FIG. 4A is equal to signal Spk(k) in FIG. 10B. As described in FIG. 10B, an adaptive filter may be utilized to determine the plant model (or plant impulse response plant(k)). In some embodiments, the plant model may be referenced as plant(k)=$m_i(k)$/y(k) or Z(plant(k))=Z($m_i(k)$)−Z(y(k)), here Z( ) represents the Z transform.

In various embodiments, remote computer 412 may store the plant model of ear cup 402 for the user, such as in a user profile. As described herein, the plant model may also be determined for a second ear cup of the headphones. So, remote computer 412 may store a user profile that may include a plant model for each ear cup of the headphones for a particular user. In some other embodiments, each ear cup may be enabled to store its corresponding plant model for one or more user profiles. In at least one of various embodiments, the headphones may include an interface (e.g., one or more buttons) to switch between different user profiles (e.g., different plant models). Similarly, the headphones may include another interface (e.g., one or more other buttons) to switch between noise environment profiles (e.g., controller designs) for a currently selected user profile.

After the plant model of ear cup 402 is determined for the particular user, system 400B of FIG. 4B may be utilized to determine the design or operating parameters (e.g., controller coefficients) of the corresponding controller for a current noise environment associated with the user. It should be noted that elements with like reference numbers in different figures may be embodiments of each other. For example, ear cup 402 in FIG. 4B may be an embodiment of ear cup 402 in FIG. 4A, remote computer 412 in FIG. 4B may be an embodiment of remote computer 412 in FIG. 4A, and so on.

As described herein, the plant model may be determined while the user is wearing the headphone in a quiet location. And the controller coefficients may be determined while the user is wearing the headphone is a location that includes the target noise environment that the user would like to cancel out. However, embodiments are not so limited, and in other embodiments, the plant model may be determined while the user is wearing the headphone in a noisy environment (which may be the target noise environment or another noise environment). In various embodiments, system 400B may be separately employed in different noise environments to determine controller coefficients for each of a plurality of different noise environment for each separate user. In various embodiments, the plant model does not need to be re-determined for each target noise environment. Rather, the plant model may be determined for separate users; separate configurations for a same user (e.g., the user with or without wearing eye glasses); from time to time (e.g., randomly or periodically) to account for wear and tear, and/or aging, of the headphones; or the like.

External microphone 404 may capture signal $m_e(k)$, which may represent the noise environment outside ear cup 402 (illustrated as noise $N_e(k)$. At the same time, internal microphone 406 may capture signal $m_i(k)$, which may represent the noise environment inside ear cup 402 (illustrated as noise $N_i(k)$. The headphones may provide signals $m_e(k)$ and $m_i(k)$ to remote computer 412. In some embodiments, ear cup 402 or the headphones may store these signals prior to providing to the remote computer.

Remote computer 412 may utilize signals $m_e(k)$ and $m_i(k)$ to determine the controller coefficients or operating parameters for the current noise environment for ear cup 402 for the user wearing the headphones. Remote computer 412 may employ embodiments described in conjunction with FIGS. 11-13 to determine the controller coefficients based on signals $m_e(k)$ and $m_i(k)$, where signal $m_i(k)$ in FIG. 4B is equal to signal $m_i(k)$ in FIGS. 11-13 and where signal $m_e(k)$ in FIG. 4B is equal to signal $m_e(k)$ in FIGS. 11-12. It should be understood that embodiments described in FIGS. 11-13 can be utilized to determine the controller coefficients for different types of controllers, such as feedforward controller, feedback controller, or hybrid feedforward-feedback controller, respectively.

In various embodiments, system 400B may be employed to determine controller coefficients for a plurality of different noise environments. For example, a user sitting in an airplane may initiate the process depicted in FIG. 4B to determine the controller coefficients for the airplane engine noise environment (assuming the plant model has already been determined for the user as depicted in FIG. 4A). The user may be enabled to save the determined controller coefficients for each ear cup of the headphones as a particular noise environment profile. In some embodiments, remote computer 412 may store one or more noise environments profiles for each of a plurality of users. The same user may later be sitting in a car and can reinitiate the process depicted in FIG. 4B to determine the controller coefficients for the road noise environment. Again, the user may be enabled to save these new controller coefficients, such as in a user profile stored on remote computer 412 (which can be utilized at a later point in time to update the controllers of the headphones without re-determining the controller coefficients and/or plant model).

After the controller coefficients for the current noise environment associated with the user are determined, system 400C of FIG. 4C may be utilized to provide the coefficients to controller 410. In various embodiments, the controller coefficients may be stored in a memory device associated with controller 410.

It should be recognized that system 400C may be utilized to provide previously determined controller coefficients to ear cup 402. In some embodiments, the user may be enabled to switch back and forth between previously saved noise environment profiles (or switch between different user profiles with different plant models of the same ear cups for different users) by employing embodiments of system 400C. For example, the user may employ a mobile application or other program/application to select a desired previously stored noise environment profile. Remote computer 412 may provide the controller coefficients that correspond to the selected noise environment profile to the headphones.

It should be also be understood that various functionality performed by the headphones and/or the remote computer, as described herein, may be interchangeable and performed on a different device. For example, in some embodiments, each ear cup of the headphones may be enabled to determine and store its corresponding plant model and/or controller design for one or more users and/or one or more noise environments (without the use of the remote computer). In other embodiments, the remote computer may be utilized to determine and store the plant models and controller designs for each ear cup. In yet other embodiments, each ear cup may determine and store a corresponding plant model, and a remote computer may store/manage a copy of the plant model, which may be utilized by the remote computer (or the headphones) to determine controller design. As such, a user interface of the headphones and/or the remote computer may enable the user to update the controller designs for each ear cup with previously determined and stored controller designs. These example embodiments should not be construed as limiting or exhaustive, but rather provide additional insight into the variety of combinations of embodiments described herein.

General Operation

The operation of certain aspects of the invention will now be described with respect to FIGS. 5-9. In at least one of various embodiments, processes 500, 600, 700, 800, and 900 described in conjunction with FIGS. 5-9, respectively, may be implemented by and/or executed on a pair of headphones (e.g., headphones 300 of FIG. 3) and/or one or more computers (e.g., remote computer 200 of FIG. 2). Additionally, various embodiments described herein can be implemented in a system such as system 100 of FIG. 1.

Figure 5:
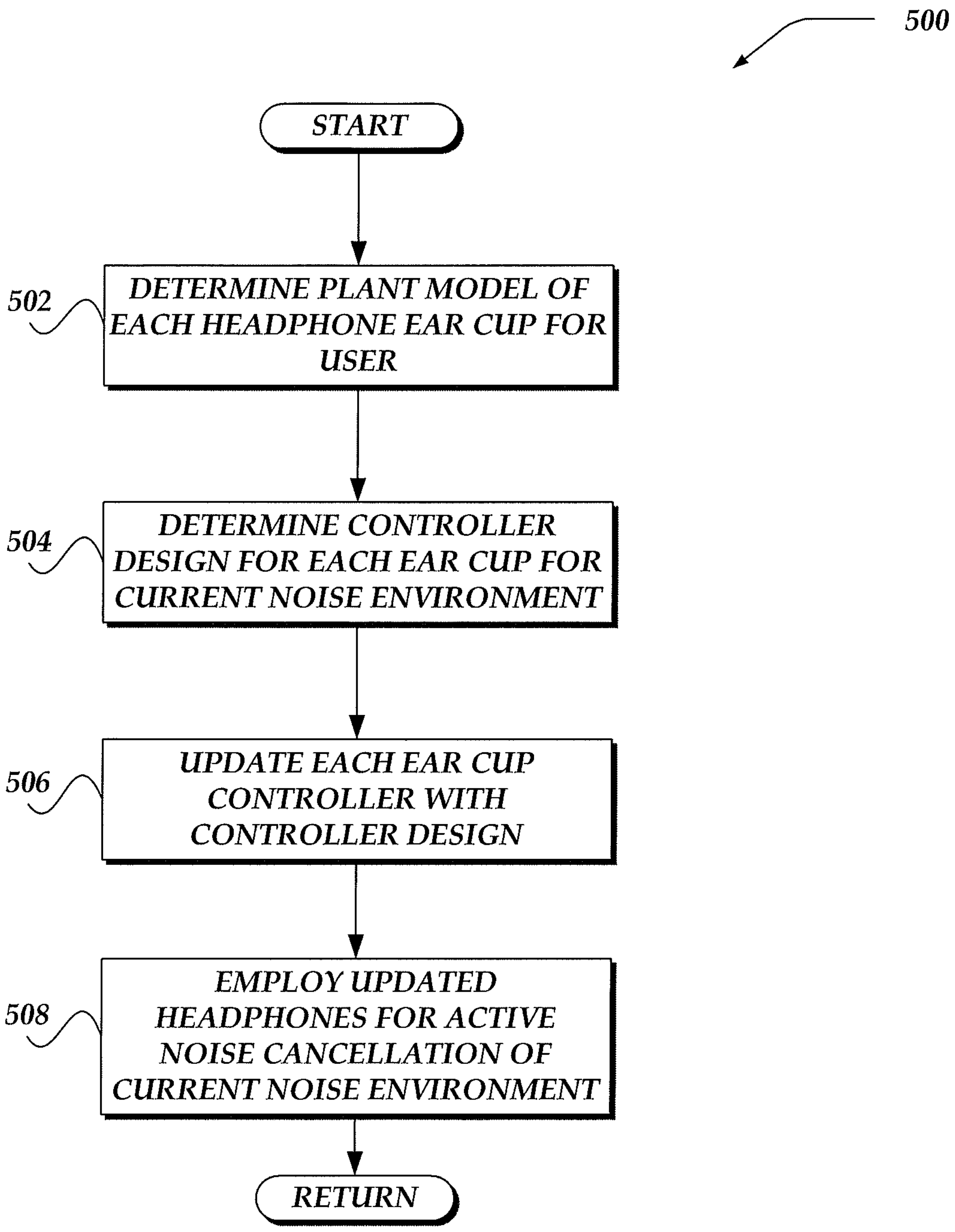
FIG. 5 illustrates a logical flow diagram generally showing one embodiment of an overview process for determining a controller design for each headphone ear cup and updating the ear cup controllers based on that design.

FIG. 5 illustrates a logical flow diagram generally showing one embodiment of an overview process for determining a controller design for each headphone ear cup and updating the ear cup controllers based on that design. Process 500 begins, after a start block, at block 502, where a plant model of each headphone ear cup may be determined for a particular user. Determining a plant model for an ear cup of the headphones used by a specific user is described in more detail below in conjunction with FIG. 6. Briefly, however, a plant model may be determined for each ear cup of the headphones for the user based on at least one reference audio signal provided by at least one speaker within each ear cup and an audio signal captured at the same time by a microphone located within each ear cup. In some embodiments, process 600 of FIG. 6 may be employed separately for each ear cup associated with the headphones while the headphones are being worn by the user in a current quiet environment.

In various embodiments, block 502 may be separately employed for each of a plurality of different users. In at least one embodiment, a separate user profile may be generated for each user of the headphones. The profile for each user may include a corresponding plant model of each ear cup of the headphones.

As users wear and use the headphones, the acoustic makeup of the headphones may change due to wear and tear on the headphones. So, in some embodiments, the plant model of each ear cup of the headphones for a user may be updated by re-employing embodiments of block 502.

Process 500 may proceed to block 504, where a design for a controller of each ear cup may be determined for a current noise environment that is associated with the user wearing the headphones. In some embodiments, determining a design for a controller may also be referred to herein as determining at least one operating parameter for a controller. In at least one of various embodiments, at least one operating parameter may include one or more coefficients that define a transfer function employed by a controller to provide active noise cancellation.

In various embodiments, the controller may be a fixed controller that can employ stored coefficients and at least one input signal to determine and/or generate a noise cancellation signal. In at least one of various embodiments, the controller may operate in a non-adaptive mode of operation. In some embodiments, the controller may be a hardware controller.

Embodiments of designing an ear cup controller are described in more detail below in conjunction with FIGS. 7 and 8. Briefly, however, at least one operating parameter may be determined for each hardware controller that corresponds to each ear cup based on at least each ear cup's corresponding plant model and at least one audio signal from the current noise environment which is captured at the same time by at least one microphone that corresponds to each ear cup. In various embodiments, one or more controller coefficients may be determined for a corresponding ear cup. In some embodiments, process 700 of FIG. 7 (or process 800 of FIG. 8) may be employed for each ear cup associated with the headphones being used by the user. In at least one of various embodiments, the controller may be a fixed active noise cancellation controller. In some embodiments, the controller may be a feedback controller, feedforward controller, or a hybrid feedback-feedforward controller.

In at least one of various embodiments, a user profile may be modified to include one or more noise environment profiles for the user that corresponds to the user profile. In various embodiments, block 504 may be separately employed for a plurality of separate and/or different noise environments. For example, block 504 may be separately employed to determine controller coefficients for "flying airplane noise," a different set of controller coefficients for "driving road noise," a third set of controller coefficients for "crowd noise," or the like. It should be understood that these environmental noises are not to be construed as limiting; but rather, a controller design (e.g., controller coefficients) may be determined for virtually any noise environment.

In other embodiments, each user profile for a plurality of users may separately include a plurality of noise environment profiles. So in some embodiments, block 504 may be employed for each separate user in different noise environments to determine the controller design for different noise environments for each user.

Although embodiments are described as the user wearing the headphones in a current noise environment for which the user would like to cancel, embodiments are not so limited. In some embodiments, the controller design for each ear cup may be determined for a target noise environment based on a simulated noise environment. In at least one of various embodiments, a remote computer may provide a simulated noise environment to the headphones (e.g., played through the speaker in the headphones and/or output by a separate speaker associated with the remote computer). In various embodiments, the simulated noise environment may be a previous audio recording of similar noise environments. In some embodiments, an application executing on the remote computer may include a plurality of simulated noise environments, including, but not limited to, subway noise, airplane engine noise, automobile road noise, or the like. In some other embodiments, the user may access other simulated noise environments on the internet, previously recorded/generated by the user, or the like.

By employing embodiments described herein using the simulated noise environment (rather than the current noise environment), the headphones can be calibrated for a particular noise environment before the user enters that noise environment. For example, if a user knows he may use the headphones in a subway at a later date/time, the user may initialize the process of determining the controller designs using a simulated subway noise environment to precompute an initial set of controller coefficients (i.e., controller design) before the user enters the subway. Once on the subway, the user may manually initiate the process for determining/updating controller coefficients, the process may be automatically initiated as a new noise environment, or the user may continue to use the precomputed controller coefficients, or the like, as described herein.

Process 500 may continue at block 506, where an operation of each ear cup controller may be updated based on the corresponding determined controller design (or operating parameters). In at least one of various embodiments, a memory (e.g., RAM) associated with each controller and/or ear cup may be modified to overwrite a previous design with a new design for the corresponding controller (e.g., the controller coefficients determined by process 700 of FIG. 7 or process 800 of FIG. 8).

As described herein, the controller coefficients may be determined on a remote computer separate from the headphones, such as, but not limited to, a smart phone, tablet computer, or other computing device (e.g., computer 200 of FIG. 2). In at least one of various embodiments, the remote computer may send and/or otherwise provide the controller coefficients for each ear cup to the headphones after they are determined by the remote computer. In at least one of various embodiments, the controller coefficients may be provided to the headphones through a wired or wireless communication technology, such as, for example, Bluetooth, Wi-Fi, or the like.

In some other embodiments, the controller coefficients may not be provided to the headphones, but may instead be maintained by the remote computer. In at least one such embodiment, the remote computer may be employed—assuming a sufficiently small latency in communications sent between the headphones and the remote computer—to determine the noise cancellation signals for the current noise environment based on the updated controller and to provide active noise cancellation.

Process 500 may proceed next to block 508, where the updated headphones may be employed to provide active noise cancellation of the current noise environment or another noise environment for at least the user. In some embodiments, the design or operating parameters (e.g., coefficients) of the controllers for each ear cup may be automatically updated based on changes in the environmental noise, which is described in more detail below in conjunction with FIG. 9.

In some embodiments, the updated headphones may be employed with another device that is different from the device utilized to determine the controller designs. For example, a user may employ a smart phone for updating the headphones, but may utilize a separate MP3 player for playing music through the updated headphones.

After block 508, process 500 may terminate and/or return to a calling process to perform other actions.

Figure 6:
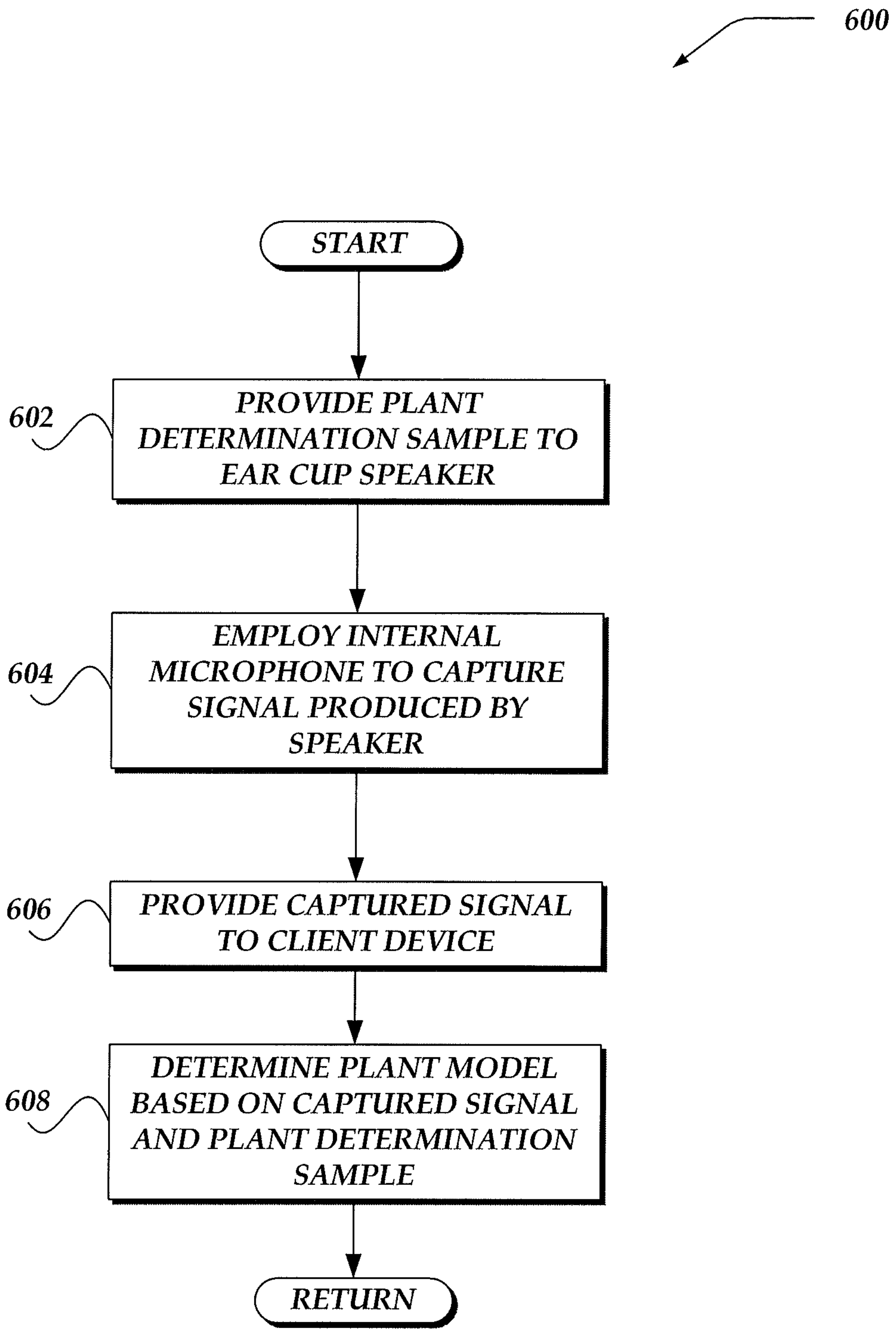
FIG. 6 illustrates a logical flow diagram generally showing one embodiment of a process for determining a plant model of a headphones' ear cup while the headphones are being worn by a user.

FIG. 6 illustrates a logical flow diagram generally showing one embodiment of a process for determining a plant model of a headphones' ear cup when the headphones are being worn by a user in a quiet noise environment. In some embodiments, process 600 may be separately employed for each different ear cup of the headphones. In other embodiments, process 600 may be employed for each different target user that may use the headphones.

In various embodiments, a user may be instructed to wear the headphones in quiet location before process 600 beings executing. In at least one of various embodiments, at least blocks 602 and 604 may be executed while the user is wearing the headphones in the quiet location.

Process 600 begins, after a start block, at block 602, where a plant determination sample signal, or reference signal, may be provided to a speaker within the ear cup of the headphones. In some embodiments, a remote computer may send and/or otherwise provide the plant determination sample signal to the headphones through a wired (e.g., transmitting an analog signal through a headphone wire using a headphone jack of the remote computer) and/or wireless communication technology (e.g., Bluetooth, Wi-Fi, or the like). In various embodiments, the plant determination sample may include various sound recordings, which may or may not be audible to the user when output by the speaker, but can be captured by a microphone that is within the ear cup.

Process 600 may proceed to block 604, where an internal microphone may be employed to capture an audio signal at the same time that the plant determination sample audio signal, or reference audio signal, is provided by the speaker. In at least one of various embodiments, this internal microphone may be internal to the ear cup and may be employed to record noise internal to the ear cup. In some embodiments, the internal microphone may be positioned approximate to the speaker, such as between the speaker and an opening of the ear cup towards the user's ear. In some embodiments, this internal microphone may be a same or different internal microphone that may be utilized to determine noise cancellation signals (e.g., if the controller is a feedback controller and/or a hybrid feedforward-feedback controller).

In any event, process 600 may continue at block 606, where the captured signal from the internal microphone may be provided to the remote computer. In some embodiments, the headphones may provide the captured signal to the remote computer in near real-time as it is captured. In other embodiments, the captured signal may be stored in a memory of the headphones prior to being provided to the remote computer. In various embodiments, the headphones may employ wired and/or wireless communication technology (e.g., Bluetooth or Wi-Fi) to provide the captured signal to the remote computer. In some embodiments, the remote computer may store the captured signal for further processing.

Process 600 may proceed next to block 608, where a plant model may be determined for the ear cup based on a comparison of the captured signal and the plant determination sample signal (i.e., reference signal). In various embodiments, the remote computer may be employed to determine the plant model. One embodiment for determining the plant model is described in more detail below in conjunction with FIGS. 10A and 10B.

After block 608, process 600 may terminate and/or return to a calling process to perform other actions.

Figure 7:
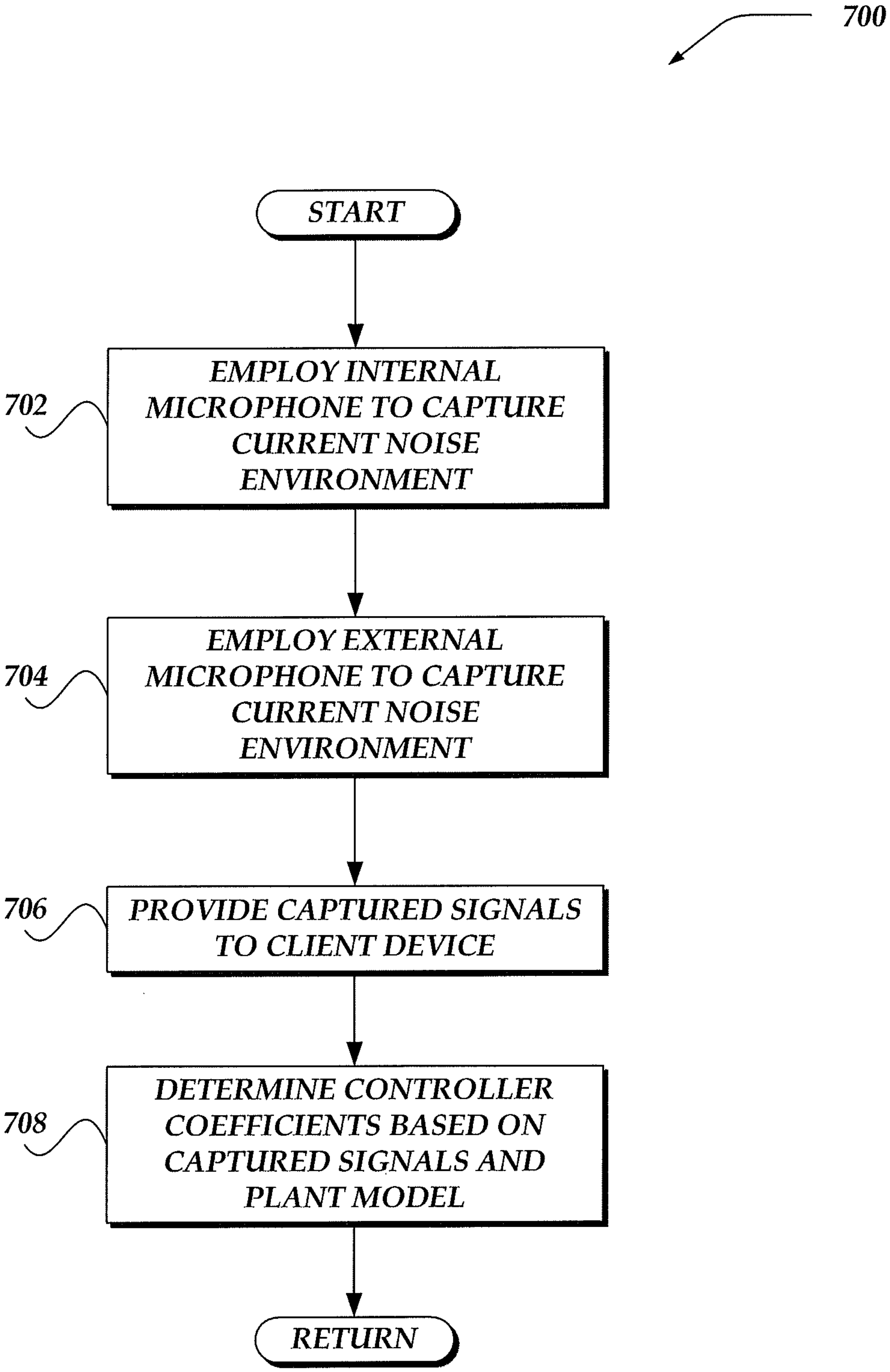
FIG. 7 illustrates a logical flow diagram generally showing an embodiment of a process for determining controller coefficients for a current noise environment that is associated with user that is wearing the headphones.

FIG. 7 illustrates a logical flow diagram generally showing an embodiment of a process for determining controller coefficients for a current noise environment that is associated with a user that is wearing the headphones. In at least one of various embodiments, process 700 may be employed to determine controller coefficients of a feedforward controller or a hybrid feedback-feedforward controller.

In some embodiments, process 700 may be separately employed for each different ear cup of the headphones. In other embodiments, process 700 may be employed for each different target noise environment in which the user may use the headphones. In various embodiments, a user may be instructed to wear the headphones in a location that includes the target noise environment that the user would like to cancel out. In at least one of various embodiments, at least blocks 702 and 704 may be executed while the user is wearing the headphones in the target noise environment. As described above, blocks 702 and 704 may be executed utilizing a simulated noise environment provided by the remote computer as the current noise environment.

Figure 11:
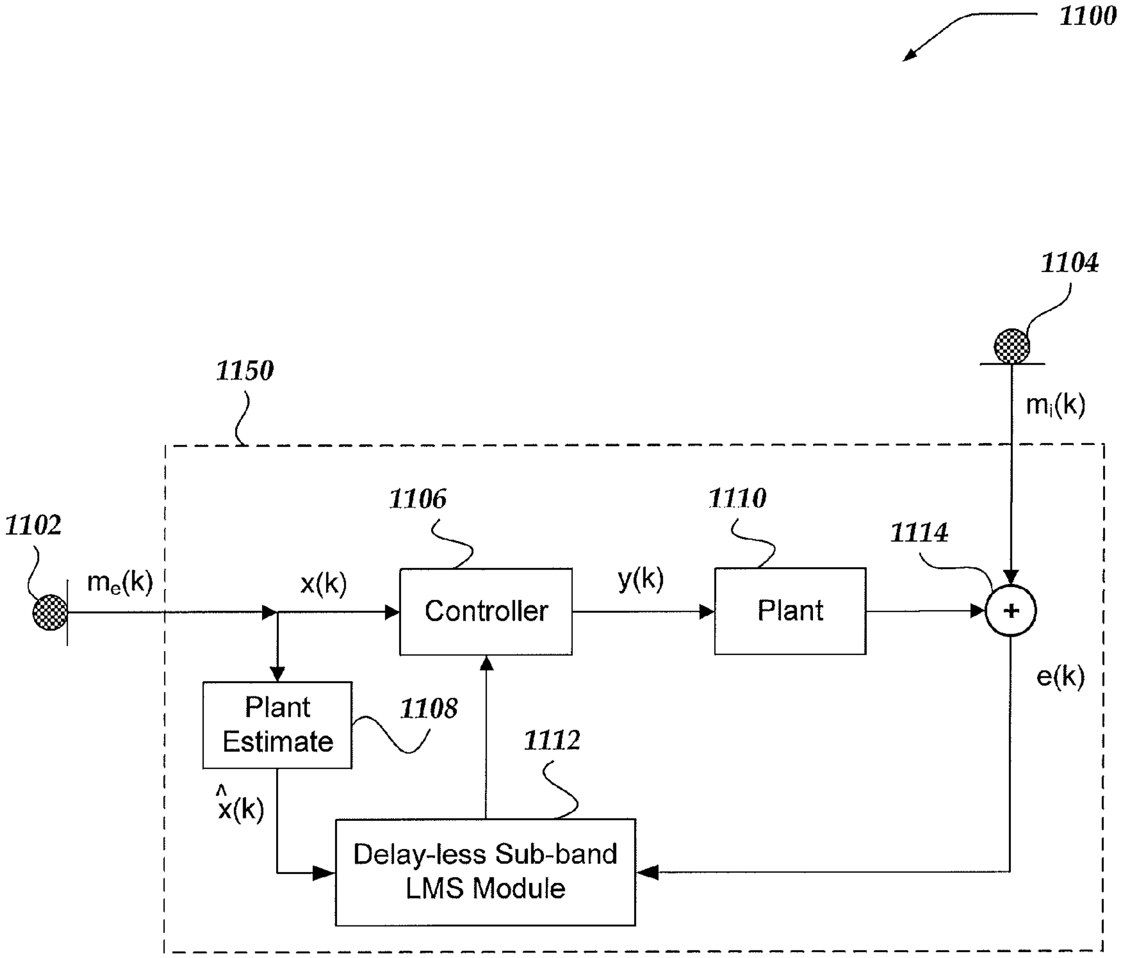
FIG. 11 illustrates a block diagram of a system for determining coefficients for a feedforward controller.
Figure 13:
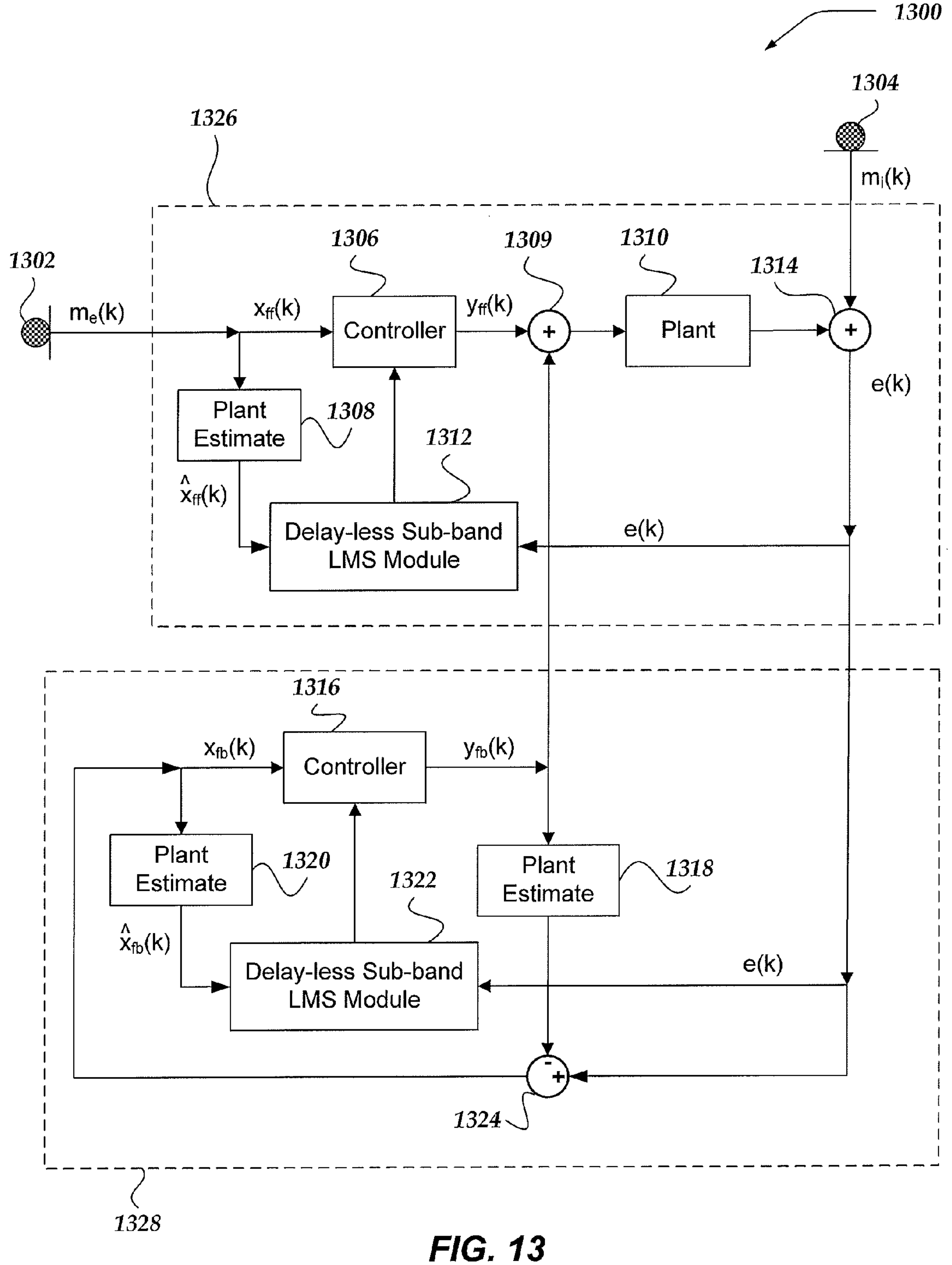
FIG. 13 illustrates a block diagram of a system for determining coefficients for a hybrid feedforward-feedback controller.

Process 700 may begin, after a start block, at block 702, where an internal microphone of an ear cup may be employed to capture a current noise environment. In some embodiments, the internal microphone may record noise internal to the corresponding ear cup. In at least one of various embodiments, the internal microphone may produce a signal that is representative of the current noise environment within the ear cup. This signal is illustrated in FIGS. 4B, 11, and 13 as signal $m_i(k)$. In some embodiments, this internal microphone may be a same microphone as is used in embodiments described in block 604 of FIG. 6.

In some embodiments, no additional noise may be provided by a speaker of the ear cup. In other embodiments, process 700 may be employed while the user is listening to music or other audio, such that the additional audio signals may be removed from the signal captured by the internal microphone.

Process 700 may proceed to block 704, where an external microphone of the ear cup may be employed to capture the current noise environment. In some embodiments, the external microphone may record noise external to the corresponding ear cup. In at least one of various embodiments, the external microphone may produce a signal that is representative of the current noise environment outside the ear cup. This signal is illustrated in FIGS. 4B, 11, and 13 as signal $m_e(k)$.

In various embodiments, the external microphone and the internal microphone may capture the current noise environment at the same time, so as to have two separate recordings of the current noise environment at the determined time intervals.

Process 700 may continue at block 706, where the captured signals may be provided to the remote computer. In at least one of various embodiments block 706 may employ embodiments of block 606 of FIG. 6 to provide signals to the remote computer.

Process 700 may proceed next to block 708, where controller coefficients for the ear cup's controller may be determined based on the captured signals and the plant model of the same ear cup (as determined at block 502 of FIG. 5). In various embodiments, the remote computer may be employed to determine the controller coefficients. One embodiment for determining the controller coefficients for a feedforward controller is described in more detail below in conjunction with FIG. 11. And one embodiment for determining the controller coefficients for a hybrid feedforward-feedback controller is described in more detail below in conjunction with FIG. 13.

After block 708, process 700 may terminate and/or return to a calling process to perform other actions.

Figure 8:
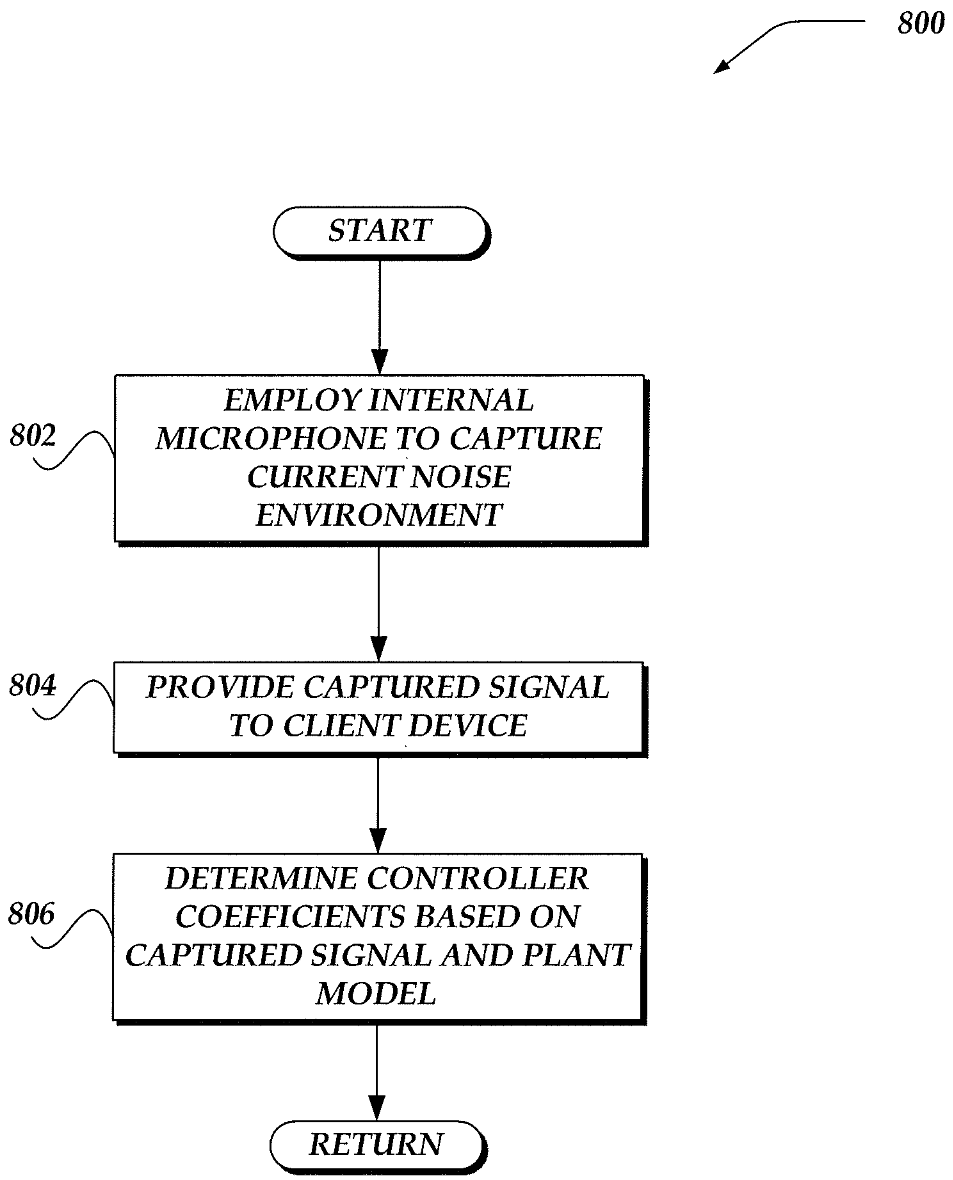
FIG. 8 illustrates a logical flow diagram generally showing an alternative embodiment of a process for determining controller coefficients for a current noise environment that is associated with user that is wearing the headphones.

FIG. 8 illustrates a logical flow diagram generally showing an alternative embodiment of a process for determining controller coefficients for a current noise environment that is associated with user that is wearing the headphones. In at least one of various embodiments, process 800 may be employed to determine controller coefficients of a feedback controller.

In some embodiments, process 800 may be separately employed for each different ear cup of the headphones. In other embodiments, process 800 may be employed for each different target noise environment in which the user may use the headphones. In various embodiments, a user may be instructed to wear the headphones in a location that includes the target noise environment that the user would like to cancel out. In at least one of various embodiments, at least block 802 may be executed while the user is wearing the headphones in the target noise environment.

Process 800 may being, after a start block, at block 802, where an internal microphone of an ear cup may be employed to capture a current noise environment. In at least one of various embodiments, block 802 may employ embodiments of block 702 of FIG. 7 to capture the current noise environment internal to the ear cup.

Process 800 may proceed to block 804, where the captured signal may be provided to the remote computer. In at least one of various embodiments, block 804 may employ embodiments of block 706 of FIG. 7 to provide the captured signal to the remote computer.

Process 800 may proceed to block 806, where controller coefficients for the ear cup's controller may be determined based on the captured signal and the plant model of the same ear cup (as determined at block 502 of FIG. 5). In at least one embodiment, the remote computer may be employed to determine the controller coefficients. One embodiment for determining the controller coefficients for a feedback controller is described in more detail below in conjunction with FIG. 12.

After block 806, process 800 may terminate and/or return to a calling process to perform other actions.

Figure 9:
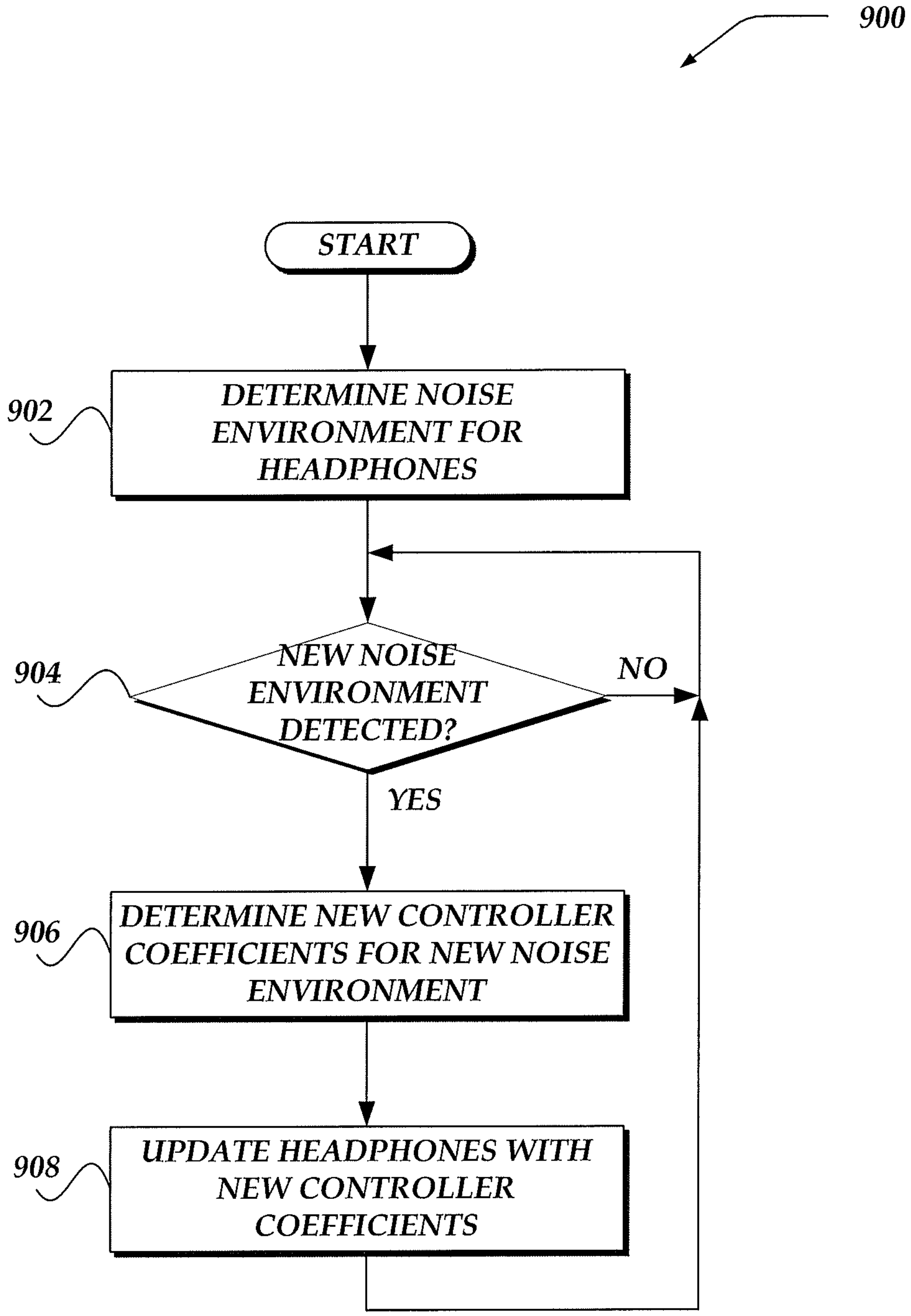
FIG. 9 illustrates a logical flow diagram generally showing one embodiment of a process for determining changes in environmental noise and automatically redesigning the controllers of the headphones' ear cups.

FIG. 9 illustrates a logical flow diagram generally showing one embodiment of a process for determining changes in environmental noise and automatically redesigning the controllers of the headphones' ear cups. Process 900 may begin, after a start block, at block 902 where a current noise environment may be determined for headphones being used by a user. In at least one of various embodiments, the current noise environment may be determined based on repetitive and/or continuous noise patterns. For example, the noise of an airplane may have one noise pattern, whereas driving road noise may have another noise pattern.

In some embodiments, the headphones may be configured based on a previously stored noise environment profile. In other embodiments, controller coefficients for the current noise environment may be automatically determined (e.g., by employing embodiments of block 504 of FIG. 5) and the headphones may be automatically updated with the controller coefficients for the current noise environment (e.g., by employing embodiments of block 506 of FIG. 5).

Process 900 may proceed to decision block 904, where a determination may be made whether a new noise environment is detected. In some embodiments, a new noise environment may be detected based on a comparison of the current noise environment to the noise environment at a previous time (e.g., if a block 902 the noise environment is stored for comparison with other noise environments). In some embodiments, various thresholds may be employed to determine if a new noise environment is detected rather than a temporary noise anomaly or deviation. For example, a new noise environment may be detected when an airplane's engines turn off (e.g., the difference between the current noise environment and a previous noise environment may be above a predetermined threshold for a predetermined period of time). In contrast, a question from a flight attendant may be an environmental noise anomaly but not a new noise environment (e.g., if the difference between the current noise environment and a previous noise environment does not continue for an amount of time exceeds a predetermined period of time).

However, alterations in the noise environment do not need to be as abrupt as an airplane's engines turning off. But rather, minor variations in the noise environment can indicate a new noise environment. For example, the noise environment may change between the airplane taxiing on the runway and flying at cruising altitude. In some embodiments, the more minor the changes in environmental noise the longer the change may be needed to be detected before determining that there is a new noise environment.

If a new noise environment is detected, then process 900 may flow to block 906; otherwise, process 900 may loop to decision block 904 to continue monitoring to detect a change in the noise environment.

At block 906, new controller coefficients may be determined for the new noise environment. In at least one of various embodiments, block 906 may employ embodiments of block 504 of FIG. 5 to design a controller for each ear cup of the headphones for the new noise environment (e.g., determine new controller coefficients).

In other embodiments, the new controller coefficients may be determined based on a set of previously determined controller coefficients. In various embodiments, a determination may be made whether the new noise environment matches a previous noise environment with previously stored controller designs. If the new noise environment matches the previous noise environment, then the new controller coefficients may be determined from a previously stored noise environment profile that corresponds to the previous/new noise environment. For example, assume a user previously determined and stored controller designs for a subway noise environment. If the user walks onto a subway and the system detects that the new noise environment matches a previously stored noise environment (i.e., the subway), then the previously stored coefficients for the previous noise environment may be loaded into the headphones (i.e., operating parameters for each controller of each ear cup may be automatically updated based on the previously stored operating parameters), instead of calculating a new set.

In at least one of various embodiments, the new noise environment may be compared to a stored sample of previous noise environments for which controller coefficients were previously determined (e.g., a noise environment profile may include a recorded sample of the noise environment in addition to the determined controller design). If the comparison is within a predetermined threshold value, then the new noise environment may be determined to match the previous noise environment.

Process 900 may proceed to block 908, where the controller of each ear cup of the headphones may be updated with the new controller coefficients. In at least one of various embodiments, block 908 may employ embodiments of block 506 of FIG. 5 to update the ear cup controllers.

After block 908, process 900 may loop to decision block 904 to detect another change in the noise environment. By looping process 900, when a new noise environment is detected, the headphones may be new controller designs may be automatically determined and the headphones automatically updated with new ear cup controller designs (e.g., new controller coefficients) based on the newly detected noise environment.

It should be understood that the embodiments described in the various flowcharts may be executed in parallel, in series, or a combination thereof, unless the context clearly dictates otherwise. Accordingly, one or more blocks or combinations of blocks in the various flowcharts may be performed concurrently with other blocks or combinations of blocks. Additionally, one or more blocks or combinations of blocks may be performed in a sequence that varies from the sequence illustrated in the flowcharts.

Further, the embodiments described herein and shown in the various flowcharts may be implemented as entirely hardware embodiments (e.g., special-purpose hardware), entirely software embodiments (e.g., processor-readable instructions), or a combination thereof. The embodiments described herein and shown in the various flowcharts may be implemented by computer instructions (or processor-readable instructions). These computer instructions may be provided to one or more processors to produce a machine, such that execution of the instructions on the processor causes a series of operational steps to be performed to create a means for implementing the embodiments described herein and/or shown in the flowcharts. In some embodiments, these computer instructions may be stored on machine-readable storage media, such as processor-readable non-transitory storage media.

Example Plant Model Determination System

Figure 10B:
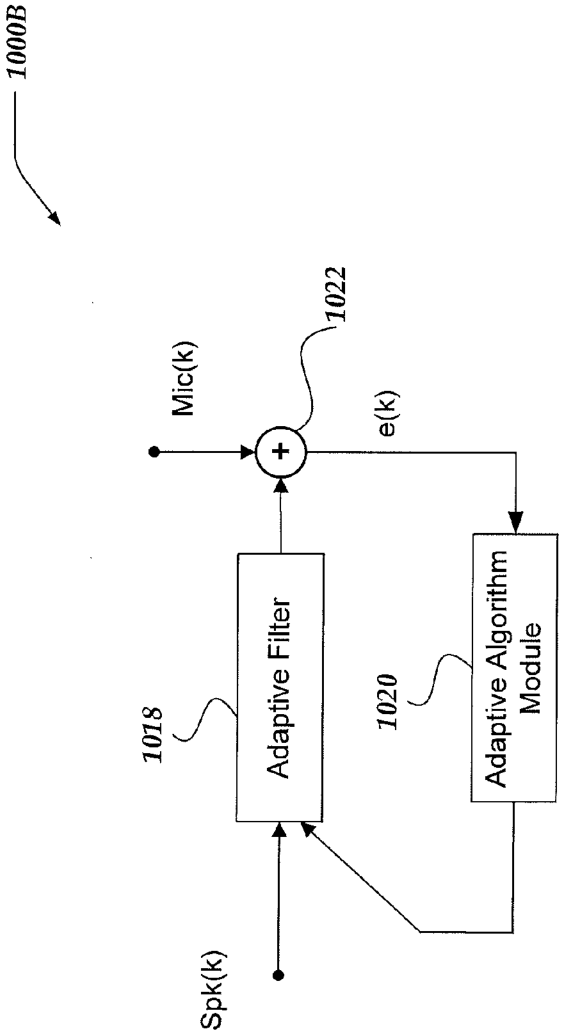

FIGS. 10A-10B illustrate block diagrams of embodiments of a system for determining a plant model for a headphone ear cup.

System 1000A may include digital-to-analog converter (DAC) 1002, reconstruction low-pass filter (LPF) 1004, power amp 1006, speaker 1008, microphone 1010, pre-amp 1012, anti-aliasing LPF 1014, and analog to digital converter (ADC) 1016.

An input signal Spk(k) may be input into DAC 1002. The output signal from the DAC may be input into reconstruction LPF 1004, the output of which may be fed into power amp 1006. The output signal from the power amp may be input into loudspeaker 1008. Microphone 1010 may record the ambient noise and the noise generated by loudspeaker 1010. The output signal of microphone 1010 may be fed into pre-amp 1012. The output from pre-amp 1012 may be input into anti-aliasing LPF 1014. The output signal from anti-aliasing LPF 1012 may be input into ADC 1016. The output signal of ADC 1016 may be signal Mic(k).

In a practical application of an adaptive controller, the use of a digital controller may utilize additional components including a DAC, ADC, reconstruction low-pass filter (LPF), an amp, and an anti-aliasing LPF. This is because whilst the controller may be digital, i.e. it operates on discrete time signals, the signal under control may be an analog signal.

The output of an ADC converter is typically a sequence of piecewise constant values. This means that it will typically contain multiple harmonics above the Nyquist frequency, and so to properly reconstruct a smooth analog signal these higher harmonics may be removed. Failure to remove these harmonics could result in aliasing. This is the role of the reconstruction low pass filter.

Aliasing is also a problem when converting the signal from analog back to digital. If the analog signal contains frequencies much higher than the sampling rate then the digitized sample may be unable to be reconstructed to the correct analog signal. To avoid aliasing, the input to an ADC can be low-pass filtered to remove frequencies above half the sampling rate. This is the role of the anti-aliasing filter.

In a practical implementation of the circuit depicted by FIG. 10A, for example in an ANC system, the signal Spk(k) could be the output of a digital controller. The z-domain transfer function from the sampled input signal Spk(k) to the sampled output signal Mic(k) may be the effective plant response seen by the digital controller. This transfer function, P(z), may corresponds to the plant response effectively seen by the digital controller. It may be the transfer function of the system under control and for digital controllers includes the impulse responses of the ADC, Reconstruction LPF, Power Amp, loudspeaker, microphone, pre-amp, anti-aliasing LPF and ADC.

A digital output signal of the plant may be Mic(k) in response to an input signal Spk(k) may be recorded. The digital input signal Spk(k) may be raw experimental data. The coefficients of the plant (i.e., the plant model) may now be calculated using an adaptive algorithm as shown by system 1000B in FIG. 10B.

The signal Spk(k) may be an input into an adaptive filter 1018. The output of the adaptive filter may be an input into summing junction 1022. At the summing junction the output of adaptive filter 1018 may be subtracted from the recorded signal Mic(k) to produce an error signal e(k). An adaptive algorithm may be used to update the coefficients of the adaptive filter in order to minimize this error signal. The adaptive algorithm may be carried out in adaptive algorithm module 1020. Adaptive algorithm module 1020 may output the values of the coefficients to the adaptive filter 1018. If coefficients are found such that the error signal is zero, then the output of the adaptive filter may be equal to the signal Mic(k), and hence the coefficients of the adaptive filter are such that the adaptive filter exactly models the plant. In practice the adaptive algorithm may run until the error signal has converged. The coefficients of the plant are found when the error signal has converged. Once the coefficients of the plant are found the corresponding transfer function of the plant can be calculated, by, for example, the equation:

$$T(z) \equiv \frac{Y(z)}{X(z)} = \sum_{i=0}^{N} b_i z^{-i}$$

where $b_i$ may be the weighting coefficients of adaptive filter 1018 in FIG. 10B).

Example Controller Coefficient Determination Systems

FIG. 11 illustrates a block diagram of a system for determining coefficients for a feedforward controller for an ear cup. In various embodiments, system 1100 of FIG. 11 may be separately employed for each separate ear cup and/or controller.

In various embodiments, microphone 1102 and microphone 1104 may be an external and internal microphone of a same ear cup (e.g., ear cup 404 of FIG. 4B), respectively. Similarly, microphone 1102 and microphone 1104 may be embodiments of external microphone 404 of FIG. 4B and internal microphone 406 of FIG. 4B, respectively. In some embodiments, the functionality of controller 1106, plant 1110, plant estimate 1108, and delay-less sub-band least mean square (LMS) Module 1112—illustrated as element 1150—may be simulated on a remote computer, such as remote computer 412 of FIG. 4B. So, in some embodiments, the remote computer may be operative to perform the actions of the components of element 1150.

Microphone 1102 may record and/or capture an external noise (e.g., an external noise environment). This noise may be converted by the microphone into a disturbance signal $m_e(k)$. In various embodiments, signal $m_e(k)$ may be provided (e.g., by Bluetooth) from the headphones (e.g., headphones 300 of FIG. 3) to a remote computer (e.g., remote computer 200 of FIG. 2). In this situation the disturbance signal $m_e(k)$ may be the reference signal x(k). The reference signal may be an input into controller 1106. In some embodiments, controller 1106 may be a simulation of an adaptive filter, such as a finite impulse response (FIR) filter, an infinite impulse response filter, or the like.

The output of controller 1106 may be signal y(k), which may be the input signal to plant 1110. In various embodiments, plant 1110 may be considered to be similar or equivalent to plant estimate 1108, which may be obtained and/or determined from the process depicted in FIGS. 10A-10B. The output of plant 1110 may be input into summing junction 1114. At the summing junction the output signal of plant 1110 and a second disturbance signal $m_i(k)$ may be summed together to produce an error signal, e(k)). The disturbance signal $m_i(k)$ may be the signal outputted from microphone 1104, which may record and/or capture the internal disturbance noise of the ear cup (i.e., the internal noise environment).

Reference signal x(k) may be input into plant estimate 1108. The output of plant estimate 1108 may be a filtered reference signal $\hat{x}(k)$. The filtered reference signal and the error signal, e(k), may be input into delay-less sub-band LMS (Least Mean Squares) module 1112. The delay-less sub-band LMS module may compute the controller coefficients and may input the values of the calculated coefficients to controller 1106. This process may run until the error signal e(k) has converged. If the error signal is zero, then the output of plant 1110 may be a signal that cancels out the disturbance signal $m_i(k)$.

In some embodiments, delay-less sub-band LMS module 1112 may employ the filtered-reference least mean square (FXLMS) algorithm. An advantage of implementing the FXLMS algorithm in sub-bands may be that it can allow the error signal to be minimized within each sub-band, allowing the noise to be attenuated across a broad band of frequency without substantially increasing the number of coefficients used in the controller. Having a large number of coefficients in the controller may utilize substantial computational effort and utilizing a sub-band structure can be a more efficient way of attenuating the noise across a broad frequency band. The number of sub-bands can depend on the sampling frequency of the system, and can increase as the sampling frequency increases.

As described herein, the determined controller coefficients may be provided from the remote computer (e.g., the device simulating controller 1106, plant 1110, plant estimate 1108, and delay-less sub-band LMS Module 1112) to the headphones for the ear cup associated with microphones 1102 and 1104.

Figure 12:
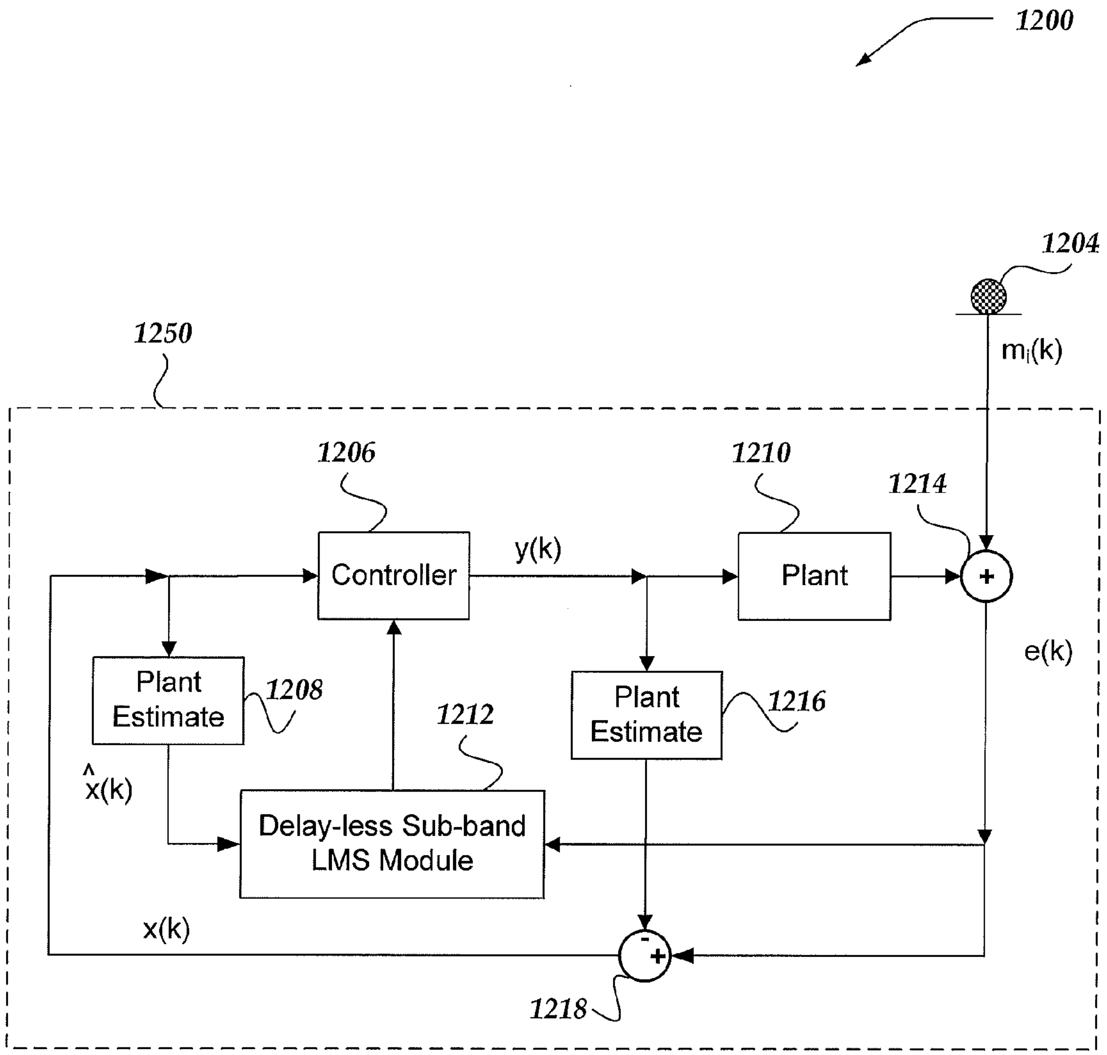
FIG. 12 illustrates a block diagram of a system for determining coefficients for a feedback controller.

FIG. 12 illustrates a block diagram of a system for determining coefficients for a feedback controller. In various embodiments, system 1200 of FIG. 12 may be separately employed for each separate ear cup and/or controller.

In various embodiments, microphone 1204 may be an internal microphone an ear cup (e.g., ear cup 404 of FIG. 4B). So, in some embodiments, microphone 1104 may be an embodiment of internal microphone 406 of FIG. 4B. In some embodiments, the functionality of controller 1206, plant 1210, plant estimate 1208, plant estimate 1216, and delay-less sub-band LMS Module 1212—illustrated as element 1250—may be simulated on a remote computer, such as remote computer 412 of FIG. 4B. So, in some embodiments, the remote computer may be operative to perform the actions of the components of element 1250.

In various embodiments, plant estimate 1208 and 1210 may be a same plant estimate and may be obtained and/or determined from the process depicted in FIGS. 10A-10B. In at least one of various embodiments, plant 1210 may be considered to be similar or equivalent to plant estimate 1208 and/or 1216.

The output of controller 1206 may be signal y(k). In some embodiments, controller 1206 may be pre-programmed to output signal y(k) in dependence on an input signal x(k−n) and pre-programmed coefficients. These coefficients may be replaced and/or modified based on the coefficients determined by delay-less sub-band LMS module 1212, as described herein. In some embodiments, controller 1206 may be a simulation of an adaptive filter, such as a finite impulse response (FIR) filter, an infinite impulse response filter, or the like.

The output signal y(k) may be input into plant 1210 and plant estimate 1216. At summing junction 1214 the output of plant 1210 and a disturbance signal $m_i(k)$ may be summed together to produce an error signal, e(k). The disturbance signal $m_i(k)$ may be the signal outputted from microphone 1204 that recorded the internal disturbance noise (e.g., noise environment inside the ear cup). The output signal of the plant estimate 1216 and the error signal may be summed together at a second summing junction 1218 to produce a reference signal x(k), which may be an estimate of the disturbance signal $m_i(k)$. The reference signal x(k) may be input into controller 1206 and a second plant estimate 1208. The output of the second plant estimate 1208 may be a filtered reference signal $\hat{x}(k)$. The filtered reference signal $\hat{x}(k)$ and the error signal e(k) may be input into delay-less sub-band LMS module 1212. The delay-less sub-band LMS module 1212 may calculate new coefficients of controller 1206 and may input these new values into controller 1206. Similar to the delay-less sub-band LMS module 1112 of FIG. 11, delay-less sub-band LMS module 1212 may employ the in sub-bands to obtain the controller coefficients. This process may run until the error signal e(k) has converged. If the error signal is zero, then the output of plant 1210 may be a signal that cancels out the disturbance signal $m_i(k)$.

FIG. 13 illustrates a block diagram of a system for determining coefficients for a hybrid feedforward-feedback controller.

System 1300 may be utilized to adaptively obtain a first and second controller for use in a hybrid ANC system. The section 1326 may be the feedforward portion of the hybrid system and section 1328 may be the feedback portion of the hybrid system.

Microphone 1302 external to the ANC system may record noise as signal $m_e(k)$. This recorded noise is used as a reference signal $x_{ff}(k)$ and may be input into controller 1306. The output of controller 1306 may be a signal $y_{ff}(k)$, which may be input into first summing junction 1309. The output signal of summing junction 1309 may be input into plant 1310. The output signal of plant 1310 may be input to second summing junction 1314. At summing junction 1314 the output signal of plant 1310 and a disturbance signal $m_i(k)$ may be summed to produce an error signal e(k). The disturbance signal may the signal that would be output by a microphone that recorded the internal disturbance noise of the ear cup. The error signal e(k) may be input into first delay-less sub-band LMS algorithm module 1312, a second delay-less sub-band LMS algorithm module 1322 and a third summing junction 1324. The feedforward reference signal $x_{ff}(k)$ may be input into first plant estimate 1308 and the output signal may be a filtered feedforward reference signal $\hat{x}_{ff}(k)$, which may be input into delay-less sub-band LMS algorithm module 1312. Delay-less sub-band LMS algorithm module 1312 may calculate new values for the coefficients of controller 1306. The updated values of the coefficients may be input to controller 1306.

A feedback reference signal $x_{fb}(k)$ may be input into second controller 1316. The output signal from controller 1316 may be a signal $y_{fb}(k)$. The output signal $y_{fb}(k)$ may be input into second plant estimate 1318 and first summing junction 1309. At the summing junction 1309 the first controller output signal $y_{ff}(k)$ may be summed with the second controller output signal $y_{fb}(k)$. At summing junction 1324 the output from plant estimate 1318 and the error signal e(k) may be summed to produce the feedback reference signal $x_{fb}(k)$. The signal $x_{fb}(k)$ may be input into third plant estimate 1320. The output of plant estimate 1320 may be a filtered feedback reference signal $\hat{x}_{fb}(k)$. This filtered reference signal may be input into delay-less sub-band LMS algorithm module 1322. Delay-less sub-band LMS algorithm module 1322 may calculate new values for the coefficients of controller 1316. The updated values of the coefficients may be input to controller 1316.

The plant coefficients used in plant estimates 1308, 1318, and 1320 in this circuit may be obtained using the method depicted in FIGS. 10A and 10B. The coefficients of the controllers used in the feedforward and feedback portions of a circuit implementing ANC may be obtained using the delay-less FXLMS adaptive algorithm in sub-bands. The fixed coefficients of the controllers 1306 and 1316 may be obtained after the convergence of the error signal. The first controller could be a finite impulse response controller. The second controller could be a finite impulse response controller. Each controller may be pre-programmed to output a signal in dependence on its input signal and its coefficients as shown by, for example, equation:

$$y(k) = \sum_{n=0}^{N-i} c_n(k)x(k-n)$$

where x(k−n) may be the input signal; $c_n(k)$, n=0, 1, . . . N−1 may be the coefficients of the controller at time k; and N may be the number of coefficients of the controller.

Illustrative Use Cases

FIGS. 14A-14D illustrate use case examples of embodiments of a graphical user interface for calibrating headphones for a user for a current noise environment.

Example 1400A may be a screenshot of a graphical user interface (GUI) for an application executing on a smart phone, tablet or other remote computer (e.g., remote computer 200 of FIG. 2). Example 1400A may enable a user to configure a noise cancellation headphone (e.g., headphones 200 of FIG. 2). Example 1400A may include at least two buttons, button 1402 and 1404. Button 1402 may enable a user to create a new user profile. In some embodiments, each new user for headphones may click on and/or otherwise select button 1402 to create their own user profile. If the user selects button 1402, then another GUI or window may open, such as example 1400B of FIG. 14B.

Button 1404 may enable a user to use, create, and/or otherwise edit a noise environment profile for a previously determined user profile. In some embodiments, each user may be enabled to use a previously determined noise environment. In other embodiments, each user may be enabled to create a new noise environment. If the user selects button 1404, then another GUI or window may open, such as example 1400C of FIG. 14C.

Figure 14B:
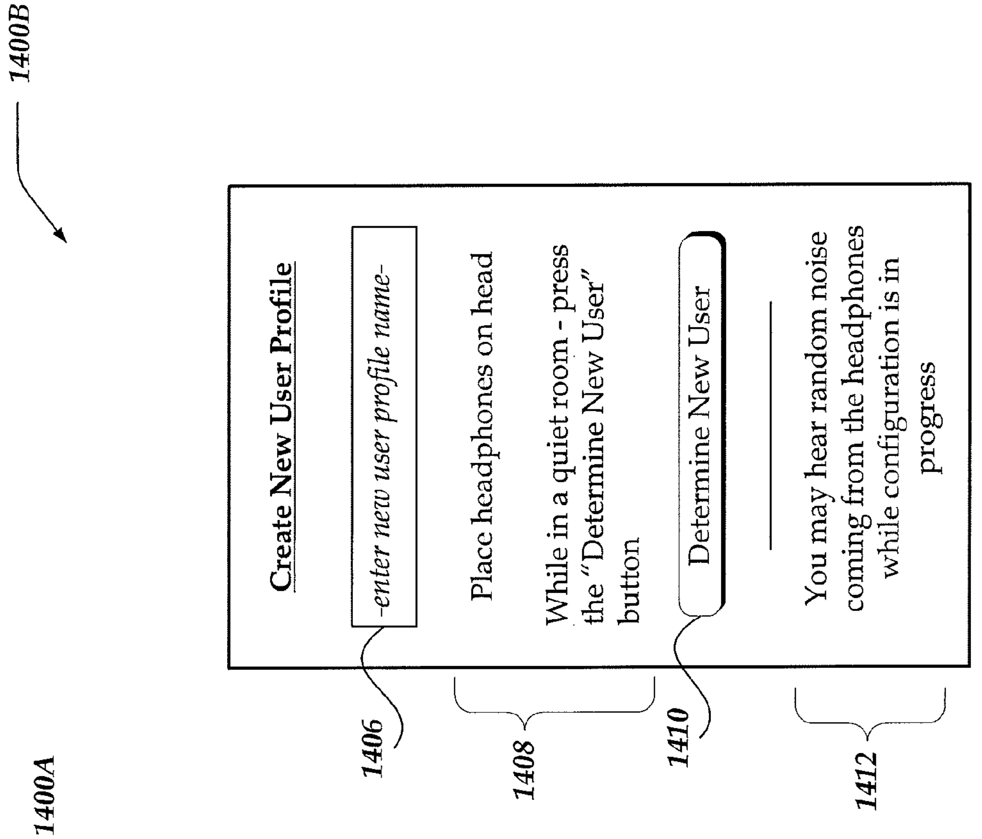
FIGS. 14A-14D illustrate use case examples of embodiments of a graphical user interface for calibrating headphones for a user for a current noise environment.
Figure 14A:
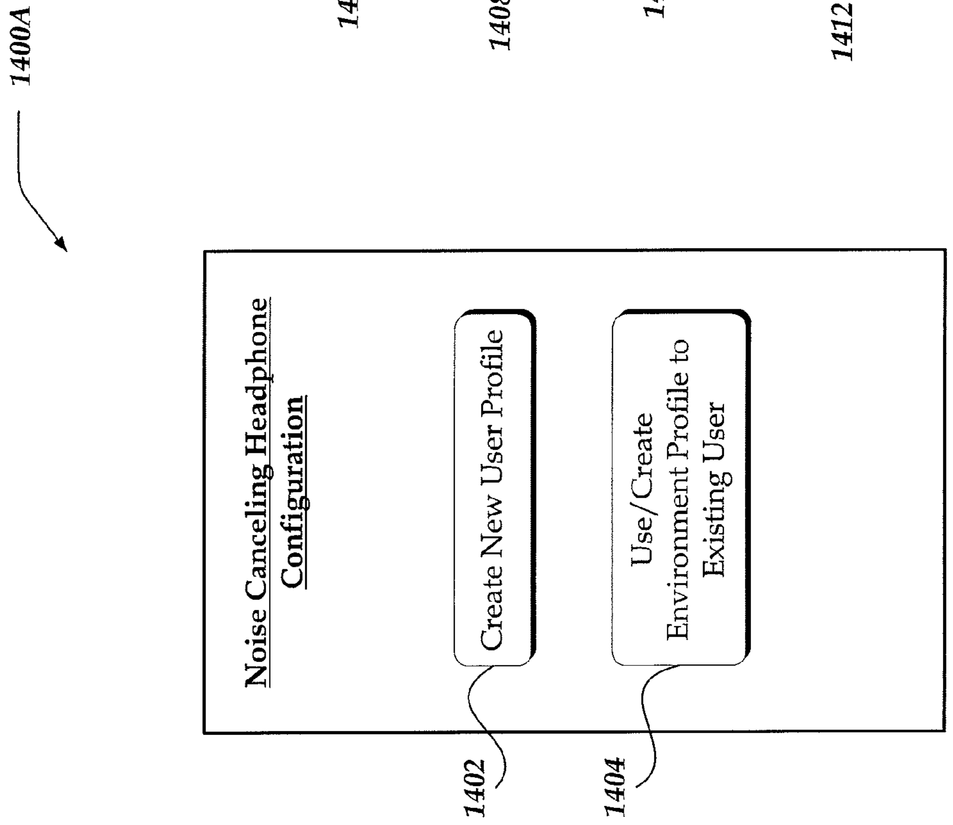
Figure 14D:
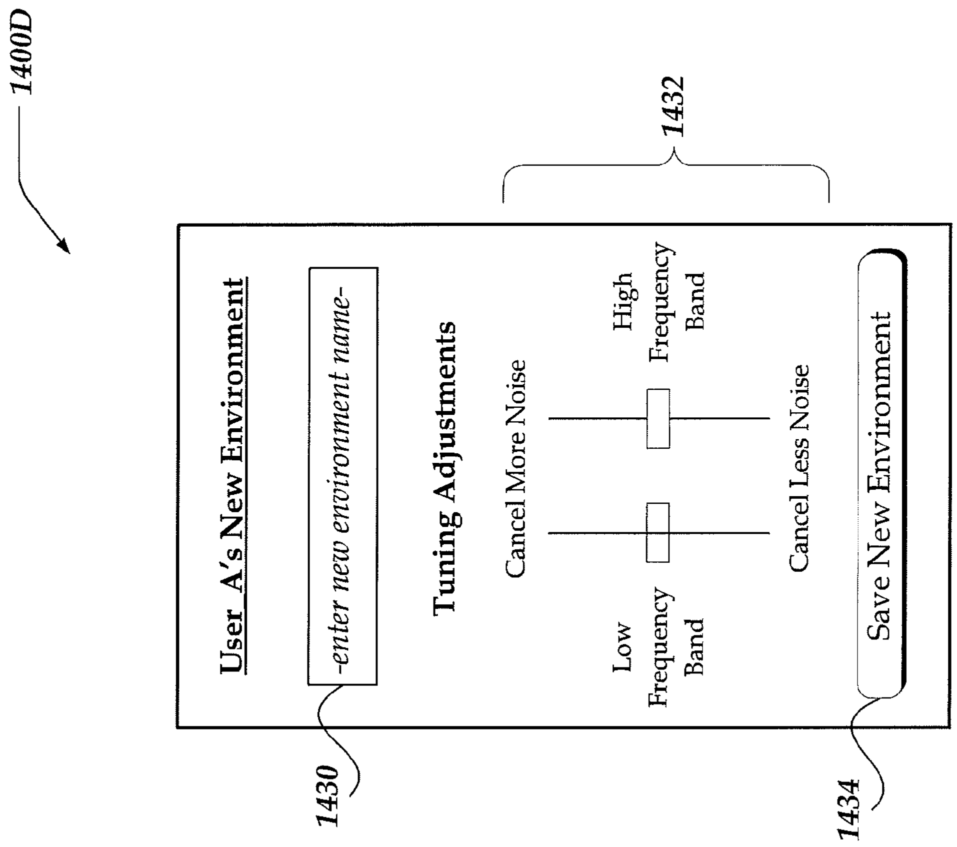
Figure 14C:
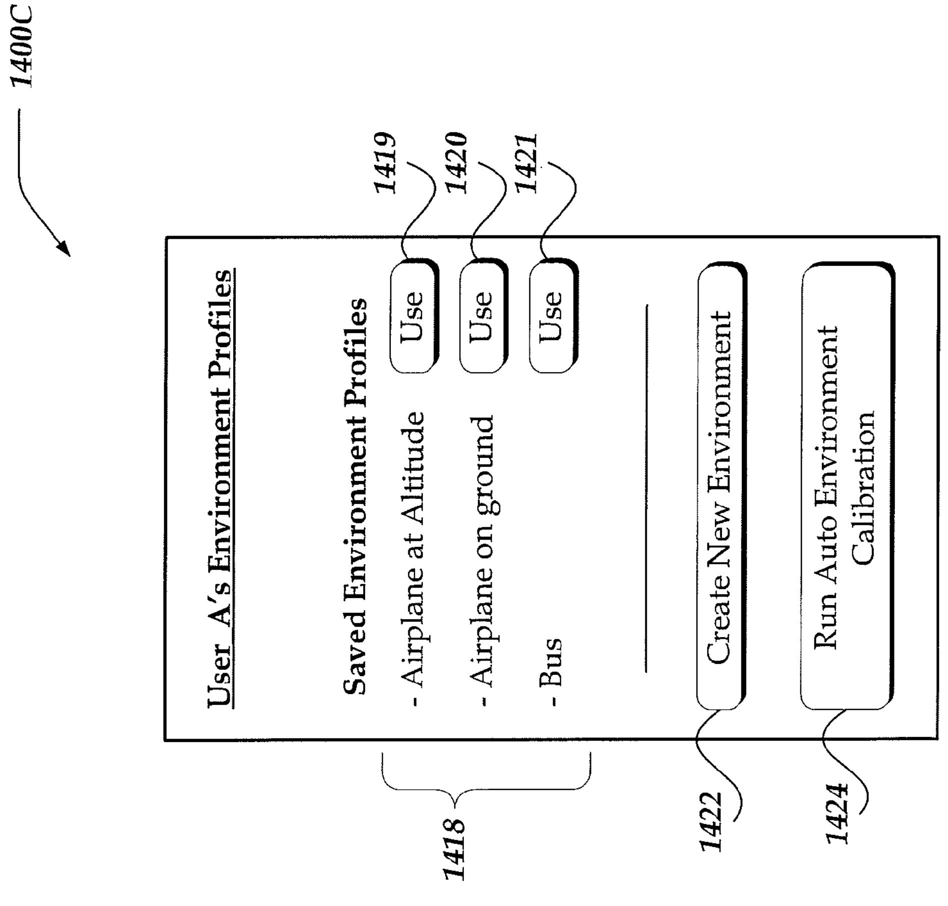

Example 1400B of FIG. 14B may be an embodiment of example 1400A, but may be a screenshot of a GUI that enables a user to create a new user profile. Input 1406 may enable the user to enter a name of the new user profile. Instructions 1408 may provide information to the user, such as “place headphones on head” and “while in a quiet room—press the ‘Determine New User’ button.” Button 1410 may be enabled to initiate the process to determine a plant model for each ear cup of the headphones, where the plant model is specific for that user. In at least one of various embodiments, selecting button 1410 may initiate the process described in conjunction with FIG. 6. Example 1400B may include other instructions, such as instructions 1412, which may provide other information to the user.

After the user profile has been created, the user can create a noise environment profile. Example 1400C of FIG. 14C may be an embodiment of example 1400A, but may be a screenshot of a GUI that enables a user to create a new noise environment profile. Environment profiles 1418 may be a list of each previously generated and/or saved noise environment profiles. In some embodiments, the user may be enabled to use and/or switch between noise environment profiles by selecting a corresponding environmental profile, such as, for example by selecting buttons 1419, 1420, or 1421. By selecting one of buttons 1419, 1420, or 1421, controller coefficients for the corresponding selected noise environment profile may be provided to the headphones, such as described above in conjunction with block 506 of FIG. 5.

A user may be enabled to create a new noise environment by clicking and/or otherwise selecting button 1422. In at least one of various embodiments, selecting button 1422 may initiate the process described in conjunction with FIGS. 7 and/or 8. In some embodiments, the user may be enabled to select button 1424 to initiate the process described in conjunction with FIG. 9 for automatically updated (and/or re-calibrating/re-configuring) the headphones based on changes in the noise environment.

After the noise environment profile has been created, the user can save the new noise environment profile. Example 1400D of FIG. 14D may be an embodiment of example 1400A, but may be a screenshot of a GUI that enables a user to save the newly created noise environment profile. The user may be enabled to input a name for the new environment profile through input 1430. In some embodiments, the user may be enabled to perform manual tuning adjustments for various frequency bands, such as by use of sliders 1432. In some embodiments, the speakers may produce a sample audio signal for which the user can hear the different in noise cancelling effects as the user adjusts sliders 1432. The user can select button 1434 to save the new noise environment profile to their profile, which once saved may be visible under profiles 1418 of FIG. 14C. Once the new environment is saved, it may be utilized update the headphones controller designs.

The above specification, examples, and data provide a complete description of the manufacture and use of the composition of the invention. Since many embodiments can be made without departing from the spirit and scope of the invention, the invention resides in the claims hereinafter appended.

What is claimed is:

1. A method for providing active noise cancellation for headphones worn by a user, comprising:

when the headphones are worn by the user in a current quiet environment, determining a plant model for each ear cup of the headphones for the user based on at least one reference audio signal provided by at least one speaker within each ear cup and an audio signal captured at the same time by a microphone located within each ear cup;

when the headphones are worn by the user in a current noise environment, determining at least one operating parameter for each controller that corresponds to each ear cup based on at least each ear cup's corresponding plant model and at least one other audio signal from the current noise environment which is captured at the same time by at least one microphone that corresponds to each ear cup;

updating at least one operation of each controller for each ear cup based on the at least one determined operating parameter for each controller; and employing the updated controllers to provide active noise cancellation when the headphones are worn by at least the user.

2. The method of claim 1, wherein updating each controller includes:

storing the at least one operating parameter of each controller in a memory corresponding to each controller.

3. The method of claim 1, wherein determining the at least one operating parameter for each controller includes:

determining at least one coefficient for a non-adaptive mode of operation for each controller, wherein the at least one coefficient defines a transfer function employed by each controller to provide the active noise cancellation.

4. The method of claim 1, wherein each controller is operable as one of a feedback controller, feedforward controller, or a hybrid feedback-feedforward controller.

5. The method of claim 1, wherein determining the plant model for each ear cup includes:

determining the plant model based on at least a comparison of the captured audio signal and the reference audio signal.

6. The method of claim 1, wherein determining the at least one operating parameter for each controller includes:

employing the microphone located within each ear cup to capture at least one current audio signal of the current noise environment within each ear cup;

employing another microphone located external to each ear cup to capture at least one other current audio signal of the current noise environment external to each ear cup; and determining the at least one operating parameter of each controller based on the plant model of each ear cup and a comparison of the at least one captured current audio signal and the at least one captured other current audio signal for each ear cup.

7. The method of claim 1, further comprising:

when a change in the current noise environment is detected, automatically determining at least one new operating parameter for each controller that corresponds to each ear cup based on at least each ear cup's corresponding plant model and at least one new audio signal from the changed current noise environment which is captured at the same time by the at least one microphone that corresponds to each ear cup; and automatically updating at least one operation of each controller for each ear cup based on the at least one new operating parameter for each controller.

8. A system for providing active noise cancellation for headphones worn by a user, comprising:

an interface device for communicating with a remote computer;

at least one ear cup that each includes at least one speaker, at least one microphone, and a controller; and a hardware processor that is operative to execute instructions that enable actions:

when the headphones are worn by the user in a current quiet environment, performing actions, including:

employing the at least one speaker of each ear cup to provide at least one reference audio signal within each ear cup and capturing an audio signal at the same time by a microphone located within each ear cup; and providing the captured audio signal to the remote computer to determine a plant model for each ear cup of the headphones for the user;

when the headphones are worn by the user in a current noise environment, performing other actions, including:

capturing at least one other audio signal from the current noise environment at the same time by the at least one microphone that corresponds to each ear cup; and providing the at least one other captured audio signal to the remote computer for use in determining at least one operating parameter for each controller that corresponds to each ear cup based on at least each ear cup's corresponding plant model and the captured at least one other audio signal for each ear cup;

updating at least one operation of each controller for each ear cup based on the at least one determined operating parameter for each controller; and employing the updated controllers to provide active noise cancellation when the headphones are worn by at least the user.

9. The system of claim 8, wherein updating each controller includes:

storing the at least one operating parameter of each controller in a memory corresponding to each controller.

10. The system of claim 8, wherein determining the at least one operating parameter for each controller includes:

determining at least one coefficient for a non-adaptive mode of operation for each controller, wherein the at least one coefficient defines a transfer function employed by each controller to provide the active noise cancellation.

11. The system of claim 8, wherein each controller is operable as one of a feedback controller, feedforward controller, or a hybrid feedback-feedforward controller.

12. The system of claim 8, wherein determining the plant model for each ear cup includes:

determining the plant model based on at least a comparison of the captured audio signal and the reference audio signal.

13. The system of claim 8, wherein determining the at least one operating parameter for each controller includes:

employing the microphone located within each ear cup to capture at least one current audio signal of the current noise environment within each ear cup;

employing another microphone located external to each ear cup to capture at least one other current audio signal of the current noise environment external to each ear cup; and determining the at least one operating parameter of each controller based on the plant model of each ear cup and a comparison of the at least one captured current audio signal and the at least one captured other current audio signal for each ear cup.

14. The system of claim 8, further comprising:

when a change in the current noise environment is detected, automatically capturing at least one new audio signal from the changed current noise environment at the same time by the at least one microphone that corresponds to each ear cup;

providing the at least one new audio signal to the network computer to automatically determine at least one new operating parameter for each controller that corresponds to each ear cup based on at least each ear cup's corresponding plant model and the at least one new audio signal for each ear cup; and automatically updating at least one operation of each controller for each ear cup based on the at least one new operating parameter for each controller.

15. A hardware chip for providing active noise cancellation for headphones worn by a user, comprising:

a communication interface that is operative to enable at least wireless communication between the headphones and a remote computer;

a processor that is operative to execute instructions that enable actions, comprising:

when the headphones are worn by the user in a current quiet environment, performing actions, including:

employing at least one speaker to provide at least one reference audio signal within each ear cup and capturing an audio signal at the same time by a microphone located within each ear cup;

providing the captured audio signal to the remote computer to determine a plant model for each ear cup of the headphones for the user;

when the headphones are worn by the user in a current noise environment, performing other actions, including:

capturing at least one other audio signal from the current noise environment at the same time by at least one microphone that corresponds to each ear cup; and providing the at least one other captured audio signal to the remote computer for use in determining at least one operating parameter for each controller that corresponds to each ear cup based on at least each ear cup's corresponding plant model and the captured at least one other audio signal for each ear cup;

updating at least one operation of each controller for each ear cup based on the at least one determined operating parameter for each controller; and employing the updated controllers to provide active noise cancellation when the headphones are worn by at least the user.

16. The hardware chip of claim 15, wherein determining the at least one operating parameter for each controller includes:

determining at least one coefficient for a non-adaptive mode of operation for each controller, wherein the at least one coefficient defines a transfer function employed by each controller to provide the active noise cancellation.

17. The hardware chip of claim 15, wherein each controller is operable as one of a feedback controller, feedforward controller, or a hybrid feedback-feedforward controller.

18. The hardware chip of claim 15, wherein determining the plant model for each ear cup includes:

determining the plant model based on at least a comparison of the captured audio signal and the reference audio signal.

19. The hardware chip of claim 15, wherein determining the at least one operating parameter for each controller includes:

employing the microphone located within each ear cup to capture at least one current audio signal of the current noise environment within each ear cup;

employing another microphone located external to each ear cup to capture at least one other current audio signal of the current noise environment external to each ear cup; and determining the at least one operating parameter of each controller based on the plant model of each ear cup and a comparison of the at least one captured current audio signal and the at least one captured other current audio signal for each ear cup.

20. The hardware chip of claim 15, further comprising:

when a change in the current noise environment is detected, automatically capturing at least one new audio signal from the changed current noise environment at the same time by the at least one microphone that corresponds to each ear cup;

providing the at least one new audio signal to the network computer to automatically determine at least one new operating parameter for each controller that corresponds to each ear cup based on at least each ear cup's corresponding plant model and the at least one new audio signal for each ear cup; and automatically updating at least one operation of each controller for each ear cup based on the at least one new operating parameter for each controller.

* * * * *